US008338482B2

(12) United States Patent
Chen et al.

(10) Patent No.: US 8,338,482 B2
(45) Date of Patent: Dec. 25, 2012

(54) MODULATING NOTCH1 SIGNALING PATHWAY FOR TREATING NEUROENDOCRINE TUMORS

(75) Inventors: Herbert Chen, Madison, WI (US); Muthusamy Kunnimalaiyaan, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 47 days.

(21) Appl. No.: 11/781,142

(22) Filed: Jul. 20, 2007

(65) Prior Publication Data
US 2008/0045445 A1 Feb. 21, 2008

(51) Int. Cl.
A61K 31/19 (2006.01)
C07C 53/128 (2006.01)

(52) U.S. Cl. ........................ 514/557; 562/400
(58) Field of Classification Search .................. None
See application file for complete search history.

(56) References Cited

U.S. PATENT DOCUMENTS

| | | | | |
|---|---|---|---|---|
| 6,905,669 B2 * | 6/2005 | DiMartino | ...................... | 424/9.1 |
| 7,154,002 B1 * | 12/2006 | Bressi et al. | ................... | 562/623 |
| 7,265,154 B2 * | 9/2007 | Gottlicher et al. | ............. | 514/560 |
| 2005/0059682 A1 * | 3/2005 | Rubinfeld | ................... | 514/263.1 |
| 2007/0190022 A1 * | 8/2007 | Bacopoulos et al. | ......... | 424/85.1 |
| 2008/0015190 A1 * | 1/2008 | Chakravarty et al. | ....... | 514/235.2 |

FOREIGN PATENT DOCUMENTS
WO WO-02/07722 A2 * 1/2002
WO WO-2007114697 A1 * 10/2007

OTHER PUBLICATIONS

Stockhausen et al. Effects of the histone deacetylase inhibitor valproic acid on Notch signalling in human neuroblastoma cells. Brit J Cancer 92: 751-759, Feb. 2005.*
Nakakura et al. Regulation of neuroendocrine differentiation in gastrointestinal carcinoid tumor cells by notch signaling. J Clin Endocrin Metab 90(7): 4350-4356, 2005.*
Kunnimalaiyaan et al. Conservation of the Notch1 signaling pathway in gastrointestinal carcinoid cells. Am J Physiol Gastrointest Liver Physiol 289: G636-G642, 2005.*
Sriuranpong et al. Notch signaling induces cell cycle arrest in small cell lung cancer cells. Cancer Res 61: 3200-3205, 2001.*
Cinatl J et al. Sodium valproate inhibits in vivo growth of human neuroblastoma cells. Anticancer Drugs 8(10):958-963, 1997.*
Baradari et al. Antiproliferative and proapoptotic effects of histone deacetylase inhibitors on gastrointestinal neuroendocrine tumor cells. Endocrine-Related Cancer 13: 1237-1250, Dec. 2006.*
Molenaar et al. The neuroendocrine and neural profiles of neuroblastomas, ganglioneuroblastomas, and ganglioneuromas. Am J Pathol 136(2): 375-382, 1990.*
Wick, M.R. Neuroendocrine Neoplasia. Am J Clin Pathol 113: 331-335, 2000.*

Jiang et al. 123I-labeled metaiodobenzylguanidine for diagnsis of neuroendocrine tumors. Reports of Med Imaging 2: 79-89, 2009.*
Kim et al. Histone deacetylase inhibitors for cancer therapy. Epigenetics 1(1): 14-23, 2006.*
McLaughlin et al. Histone deacetylase inhibitors open new doors in cancer therapy. Biochem Pharmacol 68: 1139-1144, 2004.*
Blaheta et al. Evolving anticancer drug valproic acid: insights into the mechanism and clinical studies. Med Res Rev 25(4): 383-397, Jul. 2005.*
Memon et al. Gastrointestinal carcinoid tumors. Dis Colon Rectum 40: 1101-1118, 1997.*
Kunnimalaiyaan M, Chen H. Tumor suppressor role of Notch-1 signaling in neuroendocrine tumors. Oncologist 2007; 12:535-542.
Pinchot SN, Pitt SC, Sippel RS et al. Novel targets for the treatment and palliation of gastrointestinal neuroendocrine tumors. Curr Opin Investig Drugs 2008; 9:576-582.
Shida T, Furuya M, Nikaido T et al. Aberrant expression of human achaete-scute homologue gene 1 in the gastrointestinal neuroendocrine carcinomas. Clin Cancer Res 2005; 11:450-458.
Anlauf M, Gerlach P, Schott M et al. [Pathology of neuroendocrine neoplasms]. Chirurg 2011; 82:567-573.
Kloppel G. Classification and pathology of gastroenteropancreatic neuroendocrine neoplasms. Endocr Relat Cancer 2011; 18 Suppl 1:S1-S16.
Fong KM, Sekido Y, Gazdar AF et al. Lung cancer. 9: Molecular biology of lung cancer: clinical implications. Thorax 2003; 58:892-900.
Sekido Y, Fong KM, Minna JD. Molecular genetics of lung cancer. Annu Rev Med 2003; 54:73-87.
Ball DW. Achaete-scute homolog-1 and Notch in lung neuroendocrine development and cancer. Cancer Lett 2004; 204:159-169.
Borges M, Linnoila RI, van d, V et al. An achaete-scute homologue essential for neuroendocrine differentiation in the lung. Nature 1997; 386:852-855.
Chen H, Udelsman R, Zeiger MA et al. Human achaete-scute homolog-1 is highly expressed in a subset of neuroendocrine tumors. Oncology Reports 1997; 4:775-778.
Jiang SX, Kameya T, Asamura H et al. hASH1 expression is closely correlated with endocrine phenotype and differentiation extent in pulmonary neuroendocrine tumors. Modern Pathology 2004; 17:222-229.
Jiang T, Collins BJ, Jin N et al. Achaete-scute complex homologue 1 regulates tumor-initiating capacity in human small cell lung cancer. Cancer Res 2009; 69:845-854.
Soderholm H, Ortoft E, Johansson I et al. Human achaete-scute homologue 1 (HASH-1) is downregulated in differentiating neuroblastoma cells. Biochem Biophys Res Commun 1999; 256:557-563.
Sriuranpong V, Borges MW, Strock CL et al. Notch signaling induces rapid degradation of achaete-scute homolog 1. Mol Cell Biol 2002; 22:3129-3139.
Hubaux R, Vandermeers F, Crisanti MC et al. Preclinical evidence for a beneficial impact of valproate on the response of small cell lung cancer to first-line chemotherapy. Eur J Cancer 2010; 46:1724-1734.

(Continued)

*Primary Examiner* — Bridget E Bunner
(74) *Attorney, Agent, or Firm* — Kening Li; Pinsent Masons LLP

(57) ABSTRACT

Methods and pharmaceutical compositions for treating or suppressing symptoms of neuroendocrine (NE) tumors comprising increasing the levels or activities of Notch1 protein or other components of the Notch1 signaling pathway of the cancer cells. Also disclosed are pharmaceutical compositions for the methods.

6 Claims, 18 Drawing Sheets

OTHER PUBLICATIONS

Greenblatt DY, Vaccaro AM, Juskula-Sztul R et al. Valproic acid activates notch-1 signaling and regulates the neuroendocrine phenotype in carcinoid cancer cells. Oncologist 2007; 12:942-951.

Hanna N, Bunn PA, Jr., Langer C et al. Randomized phase III trial comparing irinotecan/cisplatin with etoposide/cisplatin in patients with previously untreated extensive-stage disease small-cell lung cancer. J Clin Oncol 2006; 24:2038-2043.

Chang HH, Lee H, Hu MK et al. Notch1 expression predicts an unfavorable prognosis and serves as a therapeutic target of patietns with neuroblastoma. Clin Cancer Res 2010; 16:4411-4420.

Yao JC, Pavel M, Phan AT et al. Chromogranin A and Neuron-Specific Enolase as Prognostic Markers in Patients with Advanced pNET Treated with Everolimus. J Clin Endocrinol Metab 2011.

Kulke MH, Bendell J, Kvols L et al. Evolving diagnostic and treatment strategies for pancreatic neuroendocrine tumors. J Hematol Oncol 2011; 4:29.

Kulke MH, Siu LL, Tepper JE et al. Future directions in the treatment of neuroendocrine tumors: consensus report of the National Cancer Institute Neuroendocrine Tumor clinical trials planning meeting. J Clin Oncol 2011; 29:934-943.

Walsh KM, Choi M, Oberg K et al. A pilot genome-wide association study shows genomic variants enriched in the non-tumor cells of patients with well-differentiated neuroendocrine tumors of the ileum. Endocr Relat Cancer 2011; 18:171-180.

Kulke MH, Anthony LB, Bushnell DL et al. NANETS treatment guidelines: well-differentiated neuroendocrine tumors of the stomach and pancreas. Pancreas 2010; 39:735-752.

Klimstra DS, Modlin IR, Adsay NV et al. Pathology reporting of neuroendocrine tumors: application of the Delphic consensus process to the development of a minimum pathology data set. Am J Surg Pathol 2010; 34:300-313.

Yao JC, Lombard-Bohas C, Baudin E et al. Daily oral everolimus activity in patients with metastatic pancreatic neuroendocrine tumors after failure of cytotoxic chemotherapy: a phase II trial. J Clin Oncol 2010; 28:69-76.

Clark OH, Benson AB, III, Berlin JD et al. NCCN Clinical Practice Guidelines in Oncology: neuroendocrine tumors. J Natl Compr Canc Netw 2009; 7:712-747.

Kulke MH, Bergsland EK, Yao JC. Glycemic control in patients with insulinoma treated with everolimus. N Engl J Med 2009; 360:195-197.

Greenblatt DY, Cayo MA, Adler JT et al. Valproic acid activates Notch1 signaling and induces apoptosis in medullary thyroid cancer cells. Ann Surg 2008; 247:1036-1040.

Pinchot SN, Jaskula-Sztul R, Ning L et al. Identification and validation of Notch pathway activating compounds through a novel high-throughput screening method. Cancer 2011; 117:1386-1398.

Pinchot et al., Carcinoid Tumors. The Oncologist 2008, 13: 1255-1269.

www.cancer.gov/cancertopics/pdq/treatment/neuroblastoma/Patient/page5, lasted visited on Nov. 18, 2011.

www.cancer.gov/dictionary?CdrID=45418, lasted visited on Nov. 18, 2011.

Sethi and Kang, British Journal of Cancer advance on line publication Nov. 10, 2011; Notch signalling in cancer progression and bone metastasis.

Allenspach, Maillard, Aster and Pearl Cancer Biology & Therapy 1:5, 466-476, Sep./Oct. 2002.

Rao, 2008, Blood, 111: 477-488; Teachey et al, 2008, Blood, 111: 705-714.

Hallahan et al., The SmoA1 mouse model reveals that notch signaling is critical for the growth and survival of sonic hedgehog-induced medulloblastomas. Cancer Res., 2004, 64:7794-80.

* cited by examiner

Posterior

Anterior

Cranial

Caudal

SEQUENCE LISTING

<160> NUMBER OF SEQ ID NOS: 4

<210> SEQ ID NO 1

```
<211> LENGTH: 15
<212> TYPE: RNA
<213> ORGANISM: artificial
<220> FEATURE:
<223> OTHER INFORMATION: primer

<400> SEQUENCE: 1
ggagcccacu gcuuu                                                    15

<210> SEQ ID NO 2
<211> LENGTH: 15
<212> TYPE: RNA
<213> ORGANISM: artificial
<220> FEATURE:
<223> OTHER INFORMATION: primer

<400> SEQUENCE: 2
uccuacuaag gcugc                                                    15

<210> SEQ ID NO 3
<211> LENGTH: 15
<212> TYPE: RNA
<213> ORGANISM: artificial
<220> FEATURE:
<223> OTHER INFORMATION: primer

<400> SEQUENCE: 3
gcuacaucug gucgc                                                    15

<210> SEQ ID NO 4
<211> LENGTH: 15
<212> TYPE: RNA
<213> ORGANISM: artificial
<220> FEATURE:
<223> OTHER INFORMATION: primer

<400> SEQUENCE: 4
cacugaugca ccugu                                                    15
```

MODULATING NOTCH1 SIGNALING PATHWAY FOR TREATING NEUROENDOCRINE TUMORS

This invention was made with United States government awarded by the National Institutes of Health under the grant number:

NIH DK063015.

The United States government has certain rights in this invention.

FIELD OF THE INVENTION

This invention relates to compositions and method for treating neuroendocrine (NE) tumors by modulating the endogenous Notch1 signaling pathway of the tumor cells.

BACKGROUND OF THE INVENTION

Neuroendocrine tumors are tumors that derive from neuroectoderm, and include carcinoid tumor, and islet cell tumors. Some other types of cancers can occasionally have neuroendocrine features such as melanoma and prostate cancer. Neuroendocrine (NE) tumors, such as carcinoid, islet cell tumors, medullary thyroid cancer, small cell lung cancer, certain small intestinal cancers, pheochromocytoma, and paraganglioma, frequently metastasize to the liver, and are second only to colorectal carcinoma as the most common source of isolated hepatic metastases (Sippel and Chen, Problems in General Surgery, 2004, 20:125-133; Chen et al., J. Am. Coll. Surg., 1998, 187:88-92; Chen et al., J. Gastrointest. Surg., 1998. 2:151-155; Elias et al., J. Am. Coll. Surg., 1998, 187:487-493). Over 90% of patients with pancreatic carcinoid tumors and 50% of patients with islet cell tumors develop isolated hepatic metastases (Creutzfeldt W., 1996, World J. Surg. 20:126-131; Hiller et al., 1998, Abdom. Imaging 23:188-190; Mavligit et al., 1993, Cancer 72:375-380; Kebebew et al., 2000, Arch. Surg. 135:895-899; Isozaki et al., 1999, Intern. Med. 38:17-21). Patients with untreated, isolated NE liver metastases have less than 30% 5-year survival probability (Siperstein et al., 1990, World J. Surg. 25:693-696; Elias et al., 1998, J. Am. Coll. Surg. 187:487-493).

While surgical resection can be potentially curative, 90% of patients are not candidates for hepatectomy due to the degree of hepatic involvement by NE tumors (Nave et al., 2001, Surgery 129(2):170-175170-1755).

Besides surgery, however, there are no curative treatments for NE tumors and their hepatic metastases. Presently available alternatives to surgery, including chemoembolization, radiofrequency ablation, cryoablation, chemotherapy, and liver transplantation, have limited efficacy (Brown et al., 1999, J. Vasc. Interv. Radiol. 10:397-403; Isozaki et al., 1999, Intern. Med. 38:17-21; Miller et al., 1998, Oncol. Clin. N. Am. 7:863-879; Prvulovich et al., 1998, J. Nucl. Med. 39:1743-1745; Eriksson et al., 1998, Cancer 83:2293-2301; Lehnert T., 1998, Transplantation 66:1307-1312; Zhang et al., 1999, Endocrinology 140:2152-2158).

In general, chemotherapy has had limited success in patients with NE tumors. Multiple chemotherapeutic agents have been assessed alone or in combination for patients with advanced neuroendocrine tumors. The response rate to chemotherapy in metastatic carcinoid tumors has been reported to be no higher than about 20-30%. In endocrine pancreatic tumors, streptozocin combined with doxorubicin has been reported to generate responses in 69% of patients; however, the determination of response in this trial contained methods unacceptable to today's standards (Sippel and Chen, Problems in General Surgery 2004; 20:125-133). Of note, researchers at the Memorial Sloan-Kettering Cancer Center (MSKCC) reported a patient series treated with this regimen with a response rate of only 6% as determined by standard clinical trial criteria. The chemotherapeutic regimens recommended in neuroendocrine tumors are associated with significant toxicities. For example, the toxicities associated with streptozocin/doxorubicin include vomiting (80% of all patients, 20% severe vomiting), leukopenia (57%), renal insufficiency (44%), stomatitis, and diarrhea. Clearly in patients with a potentially indolent disease, reducing the toxicities associated with treatment is of utmost importance. Less toxic, effective therapies for this population of patients are urgently needed.

Furthermore, patients with liver metastases from NE tumors often have debilitating symptoms, such as uncontrollable diarrhea, flushing, skin rashes, and heart failure due to the excessive hormone secretion that characterizes these tumors. Thus, patients with incurable disease frequently have a poor quality of life. Therefore, for the majority of patients with NE and their hepatic metastases, there is a need for the development of other forms of therapy.

The Notch1 Signaling Pathway

Notch1 is a multi-functional transmembrane receptor that plays an important role in cellular differentiation. (Artavanis-Tsakonas S, et al. Science 1999; 284:770-776; Hald J, et al., Developmental Biology 2003; 260:426-437.) Binding of any one of the Notch ligands (Delta1 and Jagged1, for example) to Notch1 results in activation of the Notch1 protein. (Kageyama R, et al., Cell Res 1999; 9:179-188; Jarriault S, et al., Mol Cell Biol 1998; 18:7423-7431.) The activated-form of Notch1 then translocates to the nucleus and transactivates various target genes such as HES-1. (Chen H, et al., Proc Natl Acad Sci USA 1997; 94:5355-5360.)

Although dysregulation of the Notch pathway has been implicated in several neoplasms, the consequences of such dysregulation is highly cell-type specific. In other words, depending on the specific cancer type, it cannot be expected whether inhibition or activation of the Notch1 would be useful as a cancer therapeutic treatment.

For example, Notch1 has been described as a potential tumor suppressor gene in several cellular contexts. Activation of the Notch1 signaling pathway has been shown to inhibit growth and induce apoptosis in B-cells and other hematopoietic lineages in vitro. (Morimura T, et al., J Biol Chem 2000; 275:36523-36531.) Recently, Notch1 has been reported to function as a tumor suppressor in the skin. (Rangarajan A, et al., Embo Journal 2001; 20:3427-3436; Nicolas M, et al., Nature Genetics 2003; 33:416-421.) In a mouse model of basal cell carcinoma, conditional deletion of Notch1 led to an increase in the number and aggressiveness of skin carcinomas. Notch1 signaling also has been shown to inhibit growth of human hepatocellular carcinoma cells in vitro. (Qi R Z, et al., Cancer Research 2003; 63:8323-8329.) Moreover, transient expression of activated Notch1 by recombinant adenoviruses in small cell lung cancer cell lines has been shown to cause a profound growth arrest. (Sriuranpong V, et al., Cancer Research 2001; 61:3200-3205.) Therefore, these in vitro data suggest that activation of the Notch1 signaling pathway may be a potential therapeutic target for neuroendocrine (NE) tumors.

On the other hand, the constitutively activated form of Notch acts as a bona fide oncogene in leukemia and in murine breast cancer.

Nakakura et al., J. Clin. Endocrinol. Metab. 2005, 90:4350-4356) disclosed that endogenous Notch1 levels in a gastrointestinal (GI) carcinoid cell line (BON cells) was not readily detectable, but infection of the cells with an adenovirus expressing activated Notch1 resulted in accumulation of Notch protein, inhibited general NE marker expression and serotonin production, and inhibited BON cell growth.

Stockhausen et al., 2005, Brit. J. Cancer 92:751-759, discloses that in neuroblastoma (NB) cells, valproic acid (VPA) led to an activated Notch signaling cascade as shown by increased levels of intracellular Notch-1 and Hes-1, and that stimulation of NB cells with VPA led to increased cell death and phenotypic changes associated with differentiation.

However, to date, the ability of Notch1 to suppress gastrointestinal (GI) NE tumor growth has not been explored. In particular, there has been no teaching or suggestion that endogenous Notch1 signaling pathway, or components thereof, can be activated as a treatment or palliative methods for NE tumors. Although Nakakura et al. may appear to suggest that exogenous Notch1 gene may be used for treating NE tumors via gene therapy, there are many shortcomings with this approach. For examples, (1) the therapeutic DNA may be integrated in the host genome and cause mutations which may be oncogenic or otherwise deleterious; (2) the immune system of the patient will react to exogenous genes and their products, reducing the effectiveness of gene therapy, and making it difficult for gene therapy to be repeated in patients; (3) there are a number problems with viral vectors used in gene therapy, such as toxicity, immune and inflammatory responses, and gene control and targeting issues, and the possibility that the viral vector, once inside the patient, may recover its ability to cause disease.

SUMMARY OF THE INVENTION

The invention generally provides methods for inhibiting growth or neuroendocrine hormone production of a neuroendocrine (NE) tumor cell which comprises an endogenous Notch1 gene, the method comprising increasing the level of expression of the endogenous Notch1 gene. In one embodiment, the method of the present invention is used for treating neuroendocrine (NE) tumor in a patient in need thereof.

In one embodiment, a method of the present invention inhibits growth or neuroendocrine hormone production of a neuroendocrine (NE) tumor cell which comprises an endogenous Notch1 gene, and comprises increasing the level of expression of the endogenous Notch1 gene. Preferably, the expression level of the endogenous Notch 1 gene is increased.

In preferred embodimens, the method comprises contacting the cell with a histone deacetylase (HDAC) inhibitor, which may be selected from the group consisting of valproic acid (VPA), suberoylanilide hydroxamic acid (SAHA), suberic bishydroxamic acid (SBHA), Depsipeptide, Phenylbutyrate, LAQ824, PXD101, MS-275, Pyroxamide, MGCD0103BML-210, Depudecin ((2R,3S,4S,5E,7S,8S,9R)-2,9-Dihydroxy-3,4; 7,8-diepoxy-undeca-5,10-diene), HC toxin, phenylbutyrate, splitomicin, sodium butyrate, suramin sodium, and trichostatin A. Suitable NE cancer cell for the present invention include medullary thyroid cancer (MTC) cells, or gastrointestinal (GI) carcinoid cancer cells, especially those in advanced stage.

In another embodiment, the method of the present invention inhibits growth or neuroendocrine hormone production of a NE tumor cell which comprises a Notch1 signaling pathway, wherein the Notch1 signaling pathway comprises hASH1 and HES-1, wherein the Notch1 signaling pathway inhibits a Hedgehog signaling pathway which comprises Shh, PTC1, Gli1, Gli2 and Gli3, and wherein the Notch1 signaling pathway functions at least in part through a MAP kinase pathway (MAPK Pathway). The method of the present invention comprises (1) inhibiting the expression level or activity of Hash1; or (2) increasing HES1 expression or activity; or (3) decreasing the activity of the Hedgehog signaling pathway, or (4) increasing MAPK pathway signaling.

In one embodiment, the present invention provides a method for treating neuroendocrine tumor, comprising administering to a patient in need thereof an effective amount of a pharmaceutical composition comprising a histone deacetylase (HDAC) inhibitor, whereby the level of expression of an endogenous Notch1 gene in neuroendocrine tumor cells increased. In preferred embodiment, the HDAC inhibitor includes valproic acid (VPA), suberoylanilide hydroxamic acid (SAHA), suberic bishydroxamic acid (SBHA), Depsipeptide, Phenylbutyrate, LAQ824, PXD101, MS-275, Pyroxamide, MGCD0103BML-210, Depudecin ((2R,3S,4S,5E,7S,8S,9R)-2,9-Dihydroxy-3,4; 7,8-diepoxy-undeca-5,10-diene HC toxin, phenylbutyrate, splitomicin, sodium butyrate, suramin sodium, and trichostatin A.

In preferred embodiments, the method of the invention uses one or more HDAC inhibitors selected from the group consisting of SAHA, SBHA, and VPA. In one embodiment, the method of the present invention is for the treatment of a medullary thyroid cancer (MTC), or a gastrointestinal (GI) carcinoid cancer.

In another embodiment, the present invention provides a method for inhibiting growth or neuroendocrine hormone production of a neuroendocrine (NE) tumor cell which comprises a Notch1 signaling pathway, wherein the Notch1 signaling pathway comprises hASH1 and HES-1, wherein the Notch1 signaling pathway inhibits a Hedgehog signaling pathway which comprises Shh, PTC1, Gli1, Gli2 and Gli3, and wherein the Notch1 signaling pathway functions at least in part through a MAP kinase pathway (MAPK Pathway), the method comprising (1) inhibiting the expression level or activity of Hash1; or (2) increasing HES1 expression or activity; or (3) decreasing the activity of the Hedgehog signaling pathway, or (4) increasing MAPK pathway signaling. In one embodiment, the component of the Hedgehog signaling pathway is selected from the group consisting of Shh, PTC1, Gli1, Gli2 and Gli3.

In one embodiment, the method of the present invention inhibits the expression level of activity of Hash1 via an antisense nucleic acid molecule, RNAi or antibody against at least one component of the Hedgehog signaling pathway.

In another embodiment, the present invention provides a pharmaceutical composition which is formulated for treating NE tumor, comprising a histone deacetylase (HDAC) inhibitor in an amount effective for inhibiting expression of an endogenous Notch1 gene in a NE tumor cell.

BRIEF DESCRIPTION OF THE DRAWINGS

Other objects, advantages and novel features of the present invention will become apparent from the following detailed description when considered in conjunction with the accompanying drawings.

DESCRIPTION OF PREFERRED EMBODIMENTS

Figure 1:
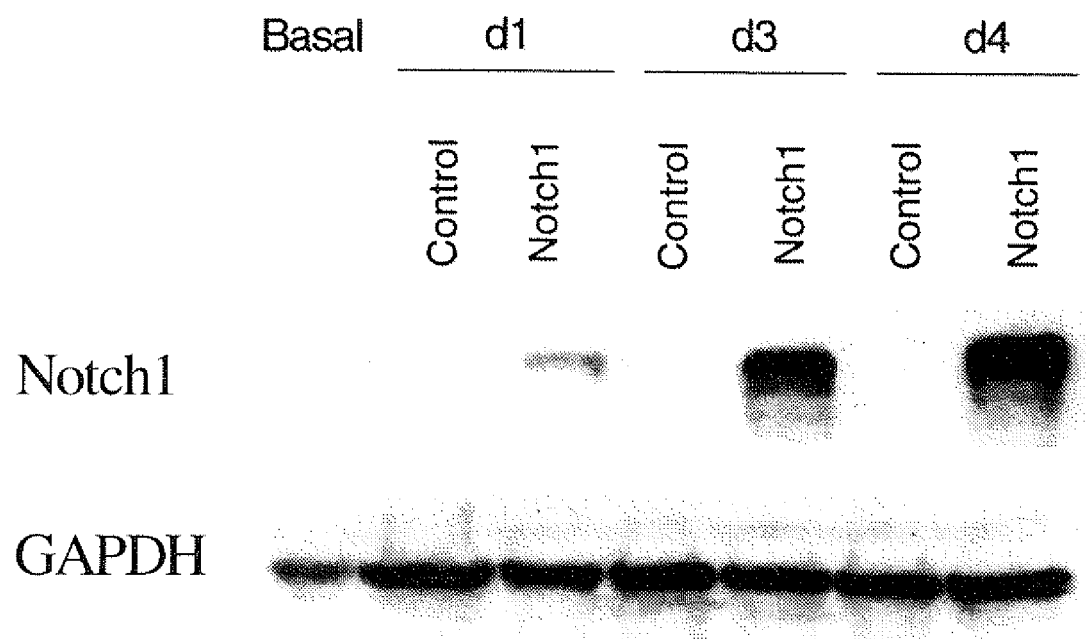
FIG. 1 is a Western analysis of BON cells for Notch1 after infection with Notch1 and control adenoviruses. GAPDH served as a loading control.

Neuroendocrine tumors arise in the neuroendocrine system and are found throughout the body, including in the lungs and gastrointestinal tract. Common NE tumors include carcinoid, gastroenteropancreatic tumors (including insulinomas, gastrinomas, glucagonomas, VIPomas (also known as Verner Morrison syndrome, and somatostatinomas. Other neuroendocrine tumors include those of the pituitary gland, melanoma, acoustic neuroma, paraganglioma, and pheochromocytoma. Pheochromocytoma is a tumor of the medulla of the adrenal glands originating in the chromaffin cells, which secretes excessive amounts of catecholamines, usually epinephrine and norepinephrine. Extra-adrenal paragangliomas (often described as extra-adrenal pheochromocytomas) are closely related, though less common, tumors that originate in the ganglia of the sympathetic nervous system and are named based upon the primary anatomical site of origin. Paragangliomas arise from the glomus cells and are closely related to pheochromocytomas. Paragangliomas are found predominantly in the abdomen (85%) and the thorax (12%), and only 3% are found in the head and neck region. Most occur as single tumors. When they occur in multiple sites they are usually found as a part of a heritable syndrome such as multiple endocrine neoplasia types II-A and II-B and Carney's complex.

The present invention provides methods of treating NE tumors via the activation of the endogenous Notch1 signaling pathway of the tumor cells. It is surprisingly discovered that in these tumor cells such activation leads to inhibition of NE tumor growth, or inhibition of NE tumor symptoms, especially hormone secretion by the tumor cells, or both.

The present inventors have discovered that Notch1 protein is not detectable in human NE tumor cells, specifically human metastatic pancreatic carcinoid cells, human pulmonary carcinoid cells, and human medullary thyroid cancer cells. The present inventors further found that Notch1 signaling is conserved in various human NE tumor cells.

In the Notch1 signaling pathway, the activated form of Notch1 translocates to the nucleus and increases expression of HES-11. HES-1, a transcriptional repressor, then inhibits expression of hASH1. In human NE tumor cell lines BON (GI carcinoid), H727 (pulmonary carcinoid), and TT (medullary thyroid cancer), induction of Notch1 all lead to reduction in hASH1 proteins and a corresponding increase in HES-1 protein. Thus, all human NE tumor cells can be treated via endogenous Notch1 activation.

The present inventors have discovered that activation of Notch1 signaling pathway suppresses the growth of NE tumor cells. For example, in vitro experiments showed that in BON cells, activation of Notch1 signaling reduced cellular proliferation rate by about 60% and similar growth suppression was seen after Notch1 induction in pulmonary H727 carcinoid cells and medullary thyroid cancer TT cells.

It has also been discovered that Notch1 activation in these cells leads to a significant decrease in hormone secretion, especially secretion of chromogranin A and synaptophysin. NE tumors typically secrete biologically active hormones and NE markers, which contribute to the virulence and metastatic potential of these malignancies. Furthermore, excessive hormone production causes significant, debilitating symptoms for patients with NE tumors, especially carcinoids. Usually, carcinoid tumors secrete high levels of both chromogranin A and serotonin due to disregulated hormone production. It has been discovered that there is a significant decrease in chromogranin A and synaptophysin levels after Notch1 activation. Similarly, over-expression of Notch1 in BON and H727 cells caused a significant reduction in serotonin secretion. Similar reductions in calcitonin production were also seen in medullary thyroid cancer TT cells after Notch1 induction.

In addition, the changes in NE marker expression in NE tumor cells correlate with the degree of Notch1 induction. For example, the levels of chromogranin A were directly proportional to the reduction in hASH1 in BON cells. At least ten (10) other primary carcinoid tumors samples [small bowel (3), appendix (2), gastric (2), rectal (2), liver metastasis (1)] were analyzed and a strong correlation between hASH1 and chromogranin A staining was found.

Accordingly, the present invention is a method for treating NE tumors by activating endogenous Notch1 signaling pathway.

By "endogenous Notch1 gene" it is meant the native Notch1 gene of a cell, which is in its normal genomic and chromatin context, and which is not heterologous to the cell. A "native chromatin environment" refers to the naturally occurring, structural relationship of genomic DNA and DNA-binding proteins (e.g., histones) which together form chromosomes. The endogenous cellular gene can be in a transcriptionally active or inactive state in the native chromatin environment.

As indicated above, the Notch1 signaling pathway comprises many components, such as Delta, Jagged, HES-1, hASH1, Notch2, Notch3, neuroD, Ngn1, Ngn2, ngn3, isl1, dll3, hey1, hey2, heyL, and Notch4, but is not active in a NE tumor cell. All necessary components of the signaling pathway, however, appear to be present in these cells and can be activated for NE tumor treatment, e.g. by contacting the cell with a suitable activator molecule.

In a preferred embodiment, the present invention provides a method for activating endogenous Notch1 signaling in a human NE cell via the use of an inhibitor of the histone deacetylases (HDAC). HDAC removes acetyl groups on histone, enabling the protein to bind to the DNA, thereby preventing transcription. HDAC inhibitors reverse these effects, allowing transcription to occur.

Many HDAC inhibitors are known and available to those skilled in the art, and many have already been used clinically or are undergoing human clinical trials. HDAC Inhibitors include suberoylanilide hydroxamic acid (SAHA), MGCD0103BML-210, suberoylanilide hydroxamic acid (SAHA), suberic bishydroxamic acid (SBHA), Depudecin ((2R,3S,4S,5E,7S,8S,9R)-2,9-Dihydroxy-3,4; 7,8-diepoxy-undeca-5,10-diene), HC toxin, phenylbutyrate, splitomicin, suberoyl bis-hydroxamic acid, sodium butyrate, suramin sodium, and trichostatin A, which are available from BIO-MOL International, L.P., Plymouth Meeting, Pa. 19462. See also those disclosed in Marks et al., Histone Deacetylase Inhibitors: Inducers of Differentiation or Apoptosis of Transformed Cells, J. Natl. Cancer Inst. 2000, 92:1210-6, and Baradari et al., Endoc. Relat. Cancer, 2006, 13:1237-50, incorporated herein by reference. Others already in clinical trials are listed in table 1 below.

TABLE 1

| HDAC inhibitors | |
| --- | --- |
| Compound | Commercial Sources |
| suberoylanilide hydroxamic acid (SAHA) | Aton Pharma (Tarrytown, NY) |
| Depsipeptide | Fujisawa (Osaka) |
| Phenylbutyrate | Elan Pharmaceuticals (Dublin) |
| LAQ824 | Novartis (Basel) |
| PXD101 | TopoTarget (Copenhagen) |
| MS-275 | Schering AG (Berlin) |
| Pyroxamide | Aton Pharma |
| MGCD0103 | MethylGene (Montreal) |

A preferred HDAC inhibitor for the present invention is valproic acid (VPA). VPA was previously found to induce differentiation of carcinoma cells, transformed hematopoietic progenitor cells and leukemic blasts from acute myeloid leukemia patients. In animal experiments, tumor growth and metastasis formation are significantly reduced with VPA treatment (Göttlicher et al., Valproic acid defines a novel class of HDAC inhibitors inducing differentiation of transformed cells EMBO J., 2001, 20, 6969-6978.) Stockhausen et al. (2005, Brit. J. Cancer 92:751-759), also discloses that in neurobalstoma (NB) cells, valproic acid (VPA) led to an activated Notch signaling cascade as shown by increased levels of intracellular Notch-1 and Hes-1, and that stimulation of NB cells with VPA led to increased cell death and phenotypic changes associated with differentiation.

The present invention further provides a pharmaceutical composition comprising an HDAC inhibitor, and a pharmaceutically acceptable excipient, for the prevention, inhibition, or treatment of NE tumors.

Administration of an "effective amount" or a "therapeutically effective amount" of an HDAC inhibitor of the present invention means an amount that is useful, at dosages and for periods of time necessary to achieve the desired result. Specifically, the HDAC inhibitor will be present in an effective amount to induce expression of Notch1 or otherwise activate the Notch1 signaling pathway in the cells being treated.

The pharmaceutical compositions according to the invention can be present and administered as liquid, semi-solid or solid medicament forms and in the form suitable for treating an NE tumor. The medicaments and pharmaceutical compositions according to the invention are prepared with the aid of agents, devices, methods and processes which are well-known in the prior art of pharmaceutical formulation, as described, for example, in "Remington's Pharmaceutical Sciences", ed. A. R. Gennaro, 17th ed., Mack Publishing Company, Easton, Pa. (1985), in particular in part 8, sections 76 to 93. The amount of active compound to be administered to the patient varies and depends on the weight, age and disease history of the patient, as well as on the mode of administration, the indication and the severity of the disease.

According to another embodiment of the present invention, the Notch1 signaling pathway may be up-regulated by manipulating the activity or level of components of the signaling pathway. For example, hASH1 and HES-1 are known components of the Notch1 signaling pathway and the present inventors have discovered that inhibiting the expression level or activity of Hash1, or increasing HES1 expression or activity will result in increased Notch1 signaling.

There is also indication that Notch1 is capable of activating the MAPK pathway in NE tumor cells. Simialrly, data suggest that the Hedgehog signaling pathway is activated in human NE tumor cells. Accordingly, in further embodiments of the present invention, methods are provided for treating NE tumors by activating the MAPK pathway, and/or decreasing the activity of the Hedgehog signaling pathway. Many methods are known and available to those skilled in the art that inhibit gene expression, e.g. via antibody, anti-sense, and RNAi.

Thus, according to one embodiment, the present invention provides a method for inhibiting growth or neuroendocrine hormone production of a neuroendocrine (NE) cancer cell which comprises a Notch1 signaling pathway, wherein the Notch1 signaling pathway comprises hASH1 and HES-1, and inhibits a Hedgehog signaling pathway which comprises Shh, PTC1, Gli1, Gli2 and Gli3, and wherein the Notch1 signaling pathway functions at least in part through a MAP kinase pathway (MAPK Pathway), the method comprising (1) inhibiting the expression level or activity of Hash1; or (2) increasing HES1 expression or activity; or (3) decreasing the activity of the Hedgehog signaling pathway, or (4) increasing MAPK pathway signaling.

Preferably, the expression level of activity of Hash1 is inhibited or decreased, for example by using an anti-hASH1 antisense nucleic acid molecule, RNAi or antibody.

In another preferred embodiment, the method of the present invention treats NE tumors via inhibiting the activity of the Hedgehog signaling pathway, e.g. by inhibiting or decreasing the level or activity of at least one component of the Hedgehog signaling pathway, for example Shh, PTC1, Gli1, Gli2 and Gli3. The expression level of Hash1, or any component thereof, may be inhibited or decreased via a suitable antisense nucleic acid molecule or RNAi, and its activity may be inhibited or decreased via an antibody.

Antibodies

In another embodiment, this invention provides neutralizing antibodies to inhibit the biological action of Hash1 protein, or a member of the Hedgehog signaling pathway ("target protein"). An antibody suitable for the present invention may be a polyclonal antibody. Preferably, the antibody is a monoclonal antibody. The antibody may also be isoform-specific. The monoclonal antibody or binding fragment thereof of the invention may be Fab fragments, F(ab)2 fragments, Fab' fragments, F(ab')2 fragments, Fd fragments, Fd' fragments or Fv fragments. Domain antibodies (dAbs) (for review, see Holt et al., 2003, Trends in Biotechnology 21:484-490) are also suitable for the methods of the present invention.

Various methods of producing antibodies with a known antigen are well-known to those ordinarily skilled in the art (see for example, Harlow and Lane, 1988, Antibodies: A Laboratory Manual. Cold Spring Harbor Laboratory Press, Cold Spring Harbor, N.Y.; see also WO 01/25437). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In accordance with the present invention, the antibodies or binding fragments thereof include those which are capable of specific binding to a target protein or an antigenic fragment thereof, preferably an epitope that is recognized by an antibody when the antibody is administered in vivo. Antibodies can be elicited in an animal host by immunization with a target protein-derived immunogenic component, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in e.g. Morrison et al., 1984, Proc. Natl. Acad. Sci. USA, 81:6851-6855; Neuberger et al., 1984, Nature, 312:604-608; and Takeda et al., 1985, Nature, 314:452-454. For human therapeutic purposes, humanized, or more preferably, human antibodies are used.

Further, single chain antibodies are also suitable for the present invention (e.g., U.S. Pat. Nos. 5,476,786 and 5,132,405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of antibodies. For example, direct injection may be suitable for delivering the antibody to the site of interest. It is also possible to utilize liposomes with antibodies in their membranes to specifically deliver the liposome to the area where target gene expression or function is to be inhibited. These liposomes can be produced such that they contain, in addition to monoclonal antibody, other therapeutic agents, such as those described above, which would then be released at the target site (e.g., Wolff et al., 1984, Biochem. et Biophys. Acta, 802:259).

Antisense Nucleic Acid Molecules

In another embodiment of the invention, antisense oligonucleotides can be used to inhibit the expression of Hash1 gene, or a gene encodes a member of the Hedgehog signaling pathway ("target gene"). The expression, preferably constitutively, of antisense RNA in cells has been known to inhibit gene expression, possibly via blockage of translation or prevention of splicing. In this regard, interference with splicing allows the use of intron sequences which should be less conserved and therefore result in greater specificity, inhibiting expression of a gene product of one species but not its homologue in another species.

The term antisense component corresponds to an RNA sequence as well as a DNA sequence, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. This antisense molecule must have sufficient complementarity, about 18-30 nucleotides in length, to the target gene so that the antisense RNA can hybridize to the target gene (or mRNA) and inhibit target gene expression regardless of whether the action is at the level of splicing, transcription, or translation. The antisense components of the present invention may be hybridizable to any of several portions of the target cDNA, including the coding sequence, 3' or 5' untranslated regions, or other intronic sequences, or to target mRNA. One of ordinary skills in the art will readily recognize that the antisense molecules can be easily designed based on the known mRNA sequences.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. In one embodiment, stable transfection and constitutive expression of vectors containing target cDNA fragments in the antisense orientation are achieved, or such expression may be under the control of tissue or development-specific promoters. Delivery can also be achieved by liposomes.

For in vivo therapy, the currently preferred method is direct delivery of antisense oligonucleotides, instead of stable transfection of an antisense cDNA fragment constructed into an expression vector. Antisense oligonucleotides having a size of 15-30 bases in length and with sequences hybridizable to any of several portions of the target cDNA, including the coding sequence, 3' or 5' untranslated regions, or other intronic sequences, or to target mRNA, are preferred. Sequences for the antisense oligonucleotides to target are preferably selected as being the ones that have the most potent antisense effects. Factors that govern a target site for the antisense oligonucleotide sequence include the length of the oligonucleotide, binding affinity, and accessibility of the target sequence. Sequences may be screened in vitro for potency of their antisense activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred target antisense oligonucleotides are those oligonucleotides which are stable, have a high resistance to nucleases, possess suitable pharmacokinetics to allow them to traffic to target tissue site at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNase H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

The delivery route will be the one that provides the best antisense effect as measured according to the criteria described above. In vitro and in vivo assays using antisense oligonucleotides have shown that delivery mediated by cationic liposomes, by retroviral vectors and direct delivery are efficient. Another possible delivery mode is targeting using antibody to cell surface markers for the target cells. Antibody to target or to its receptor may serve this purpose.

RNAi

In a further embodiment, the expression of Hash1 gene, or a gene that encodes a member of the Hedgehog signaling pathway may be inhibited by small interfering RNAs (siRNA, also known as RNAi, RNA interference nucleic acids). siRNA are double-stranded RNA molecules, typically 21 n.t. in length, that are homologous to the target gene and interfere with the target gene's activity.

siRNA technology relates to a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the siRNA (sequence-specific) pathway, the initiating dsRNA is first broken into short interfering (si) RNAs, as described above. The siRNAs have sense and antisense strands of about 21 nucleotides that form approximately 19 nucleotide siRNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411:494-8). siRNA has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al., 2001, Genes Dev. 15:188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al., 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent preferred segments of the mRNA to target for siRNA, ribozyme or antisense technologies. Accordingly, preferred segments of the mRNA target can be identified for design of the siRNA mediating dsRNA oligonucleotides as well as for design of appropriate ribozyme and hammerheadribozyme compositions of the invention (see below).

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74). The effectiveness of the siRNA may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of siRNA technology are provided in U.S. patent application Ser. Nos. 6,278,039, 5,723,750 and 5,244,805, which are incorporated herein by reference.

The following examples are intended to illustrate preferred embodiments of the invention and should not be interpreted to limit the scope of the invention as defined in the claims.

EXAMPLES

Example 1

Notch1 Expression in Human NE Cells

Three NE tumor cell lines, i.e., a human metastatic pancreatic carcinoid cell line, BON, (Evers B M, et al., Gastroenterology 1991; 101:303-311) a human pulmonary carcinoid cell lines H727, (Borges M, et al., Nature 1997; 386:852-855) and a human medullary thyroid cancer cell line TT, (Chen H, et al., Surgery 1996; 120:168-172) were used to study the biological consequences of Notch1 activation in NE tumors in vitro. In order to determine the effect of Notch1 overexpression in BON cells, high titer recombinant adenoviruses were used. Briefly, an intracellular Notch1 fragment, containing residues 1759-2556, was cloned into a pAdTrackCMV shuttle plasmid and then co-transfected with pAdEASY1 into BJ5183 bacterial competent cells to generate recombinant adenoviruses. As a control, the *E. coli* beta-galactosidase (B-gal) gene was also cloned into shuttle plasmids. Notch1 and B-gal containing adenoviruses were used to infect BON cells. BON cells normally lack Notch1 protein by Western analysis (FIG. 1). However, infection with Notch1 adenoviruses led to high levels of Notch1 that was not seen with infection with β-gal control adenoviruses (FIG. 1). We have also observed that Notch1 protein is not detectable in pulmonary carcinoid H727 cells and medullary thyroid cancer TT cells

Example 2

The Notch1 Signaling Pathway Is Conserved in Human NE Tumor Cells

Figure 2:
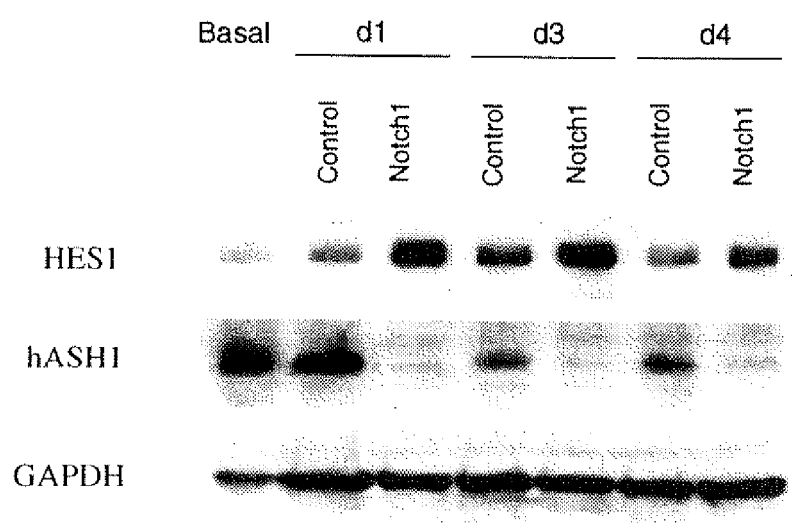
FIG. 2 is a Western analysis of BON cells for hASH1 and HES-1 after infection with Notch1 and control adenoviruses. GAPDH served as a loading control.

As discussed above, the activated form of Notch1 translocates to the nucleus and increases expression of HES-1. (Artavanis-Tsakonas S, et al., Science 1999; 284:770-776) HES-1, a transcriptional repressor, then inhibits expression of hASH1. BON, H727, and TT cells were analyzed for their hASH1 expression and HES-1 levels after induction of Notch1. As shown in FIG. 2, BON cells normally express high levels of hASH1 and detectable levels of HES-1 protein. However, increased Notch1 activity led to a dramatic reduction in hASH1 proteins by 24 hours that was not seen in the control. In addition, there was a corresponding increase in HES-1 protein. Similar changes were also seen with Notch1 activation in pulmonary carcinoid H727 and medullary thyroid cancer TT cells (not shown). Therefore, the Notch1 signaling pathway is conserved in human NE tumors cells.

Example 3

Notch1 Regulates The Endocrine Phenotype of NE Tumor Cells

Figure 3:
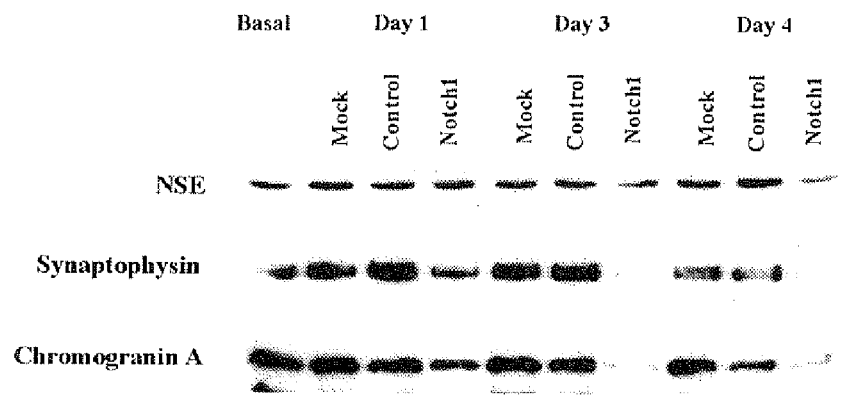
FIG. 3 is a Western analysis of BON cells for synaptophysin, neuron-specific enolase (NSE), and chromogranin A at baseline (mock) and after infection with Notch1 and control adenoviruses.
Figure 4:
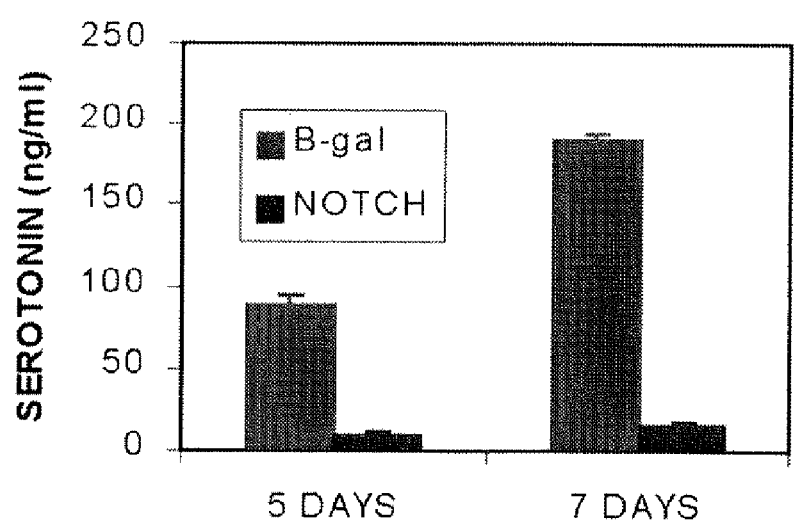
FIG. 4 shows a serotonin ELISA of BON cells after infection with Notch1 and β-gal adenoviruses.

NE tumors typically secrete biologically active hormones and NE markers, which are thought to contribute to the virulence and metastatic potential of these malignancies. (von Wichert G, et al., Cancer Res 2000; 60:4573-4581; Eriksson B, et al., Digestion 2000; 62 Suppl 1:33-38) Furthermore, excessive hormone production causes significant, debilitating symptoms for patients with NE tumors, especially carcinoids. Notch1 signaling plays an essential role in the endocrine differentiation of the GI tract. (Artavanis-Tsakonas S, et al., Science 1999; 284:770-776; Jensen J, et al., Diabetes 2000; 49:163-176; Apelqvist A, et al., Nature 1999; 400:877-881) Usually, carcinoid tumors secrete high levels of both chromogranin A and serotonin due to disregulated hormone production. Similarly, BON and H727 cells had high levels of the NE marker chromogranin A by Western analysis. However, a significant decrease in chromogranin A and synaptophysin levels after Notch1 activation in these cells observed (FIG. 3). In addition, the carcinoid cell lines were tested for serotonin secretion by ELISA after Notch1 induction. Similarly, overexpression of Notch1 in BON and H727 cells caused a significant reduction in serotonin secretion (FIG. 4). Similar reductions in calcitonin production were also seen in medullary thyroid cancer TT cells after Notch1 induction (not shown).

Example 4

Figure 5:
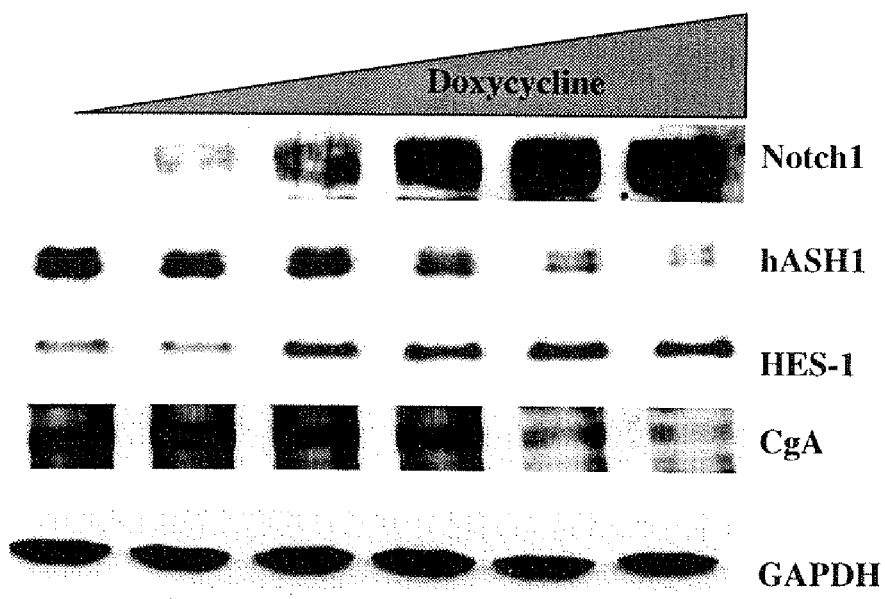
FIG. 5 shows that exposure to increasing concentrations of tetracycline led to increasing expression of Notch1 protein and the changes in hASH1 and NE marker expression in NE tumor cells correlate with the degree of Notch1 induction.

Changes in Hash1 and NE Marker Expression Correlate With the Degree of Notch1 Induction TET-Notch1 vectors were stably transfected into human NE tumor cells lines BON (GI carcinoid), H727 (pulmonary carcinoid) and TT (medullary thyroid cancer) creating BON-Notch1, H727-Notch1, and TT-Notch1 cells. The cells were then treated with increasing concentrations of tetracycline and analyzed the cellular lysates for Notch1, HES-1, hASH1, and the NE marker chromogranin A. As shown in FIG. 5, exposure to increasing concentrations of tetracycline led to increasing expression of Notch1 protein. This tetracycline dose-dependent induction of Notch1 led to progressive reductions in hASH1, and importantly, the levels of chromogranin A were directly proportional to the reduction in hASH1. Thus, the changes in hASH1 and NE marker expression in NE tumor cells correlate with the degree of Notch1 induction.

Figure 6:
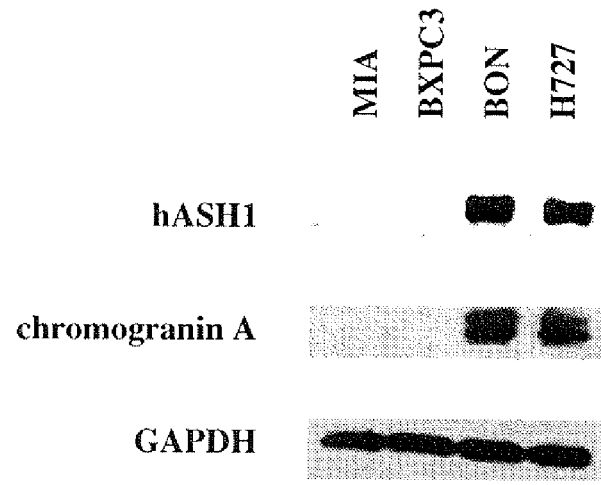
FIG. 6 shows hASH1 levels correlate with chromogranin A in human tumor cell lines.
Figure 7:
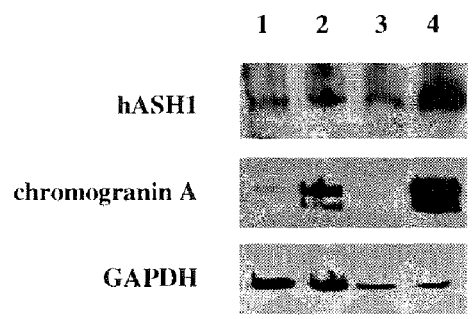
FIG. 7 shows that hASH1 levels correlate with chromogranin A in human carcinoid tumors.
Figure 8:
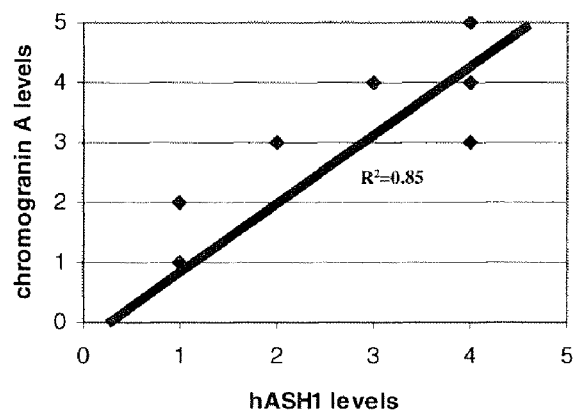
FIG. 8 shows strong correlation between hASH1 and chromogranin A levels in 10 primary and metastatic carcinoid tumors.

Example 5 hASH1 Protein Expression is Directly Related to NE Marker Levels in Tumor Cells Lines and Carcinoid Tumors Various human NE tumor cell lines, including GI carcinoid BON, pulmonary carcinoids H727 and H720, medullary thyroid cancer (TT), and pheochromocytoma SW13, were analyzed for hASH1 and NE marker expression by Western blot. All human NE cell lines studied express high levels of hASH1 protein and NE markers (chromogranin A, neuron-specific enolase, and synaptophysin). In contrast, pancreatic adenocarcinomas MIA and BXPC3, embryonal kidney HEK293, and colon adenocarcinoma RKO cell lines lack hASH1 protein and NE markers (FIG. 6 and Chen H, et al., Cell Growth Differ 1997; 8:677-686).

hASH1 levels have also been found to correlate with NE marker expression in human tumor tissue. We analyzed 4 human GI carcinoid tumors for hASH1 and chromogranin A expression by Western blot (FIG. 7). hASH1 protein also appeared to correlate with the level of chromogranin A expression in these human tumor samples. In parallel to our analysis of fresh frozen NE tumors by Western blot, we have successfully utilized a hASH1 antibody for immunohistochemistry on paraffin-embedded carcinoid tumor samples. Ten (10) primary carcinoid tumors from our archival, paraffin-embedded carcinoid tumor samples [small bowel (3), appendix (2), gastric (2), rectal (2), liver metastasis (1)] were analyzed and a strong correlation between hASH1 and chromogranin A staining (FIG. 8). Thus, hASH1 may play a role in the NE phenotype of human NE tumors.

Example 6

Notch1 Induction Suppresses Growth of NE Tumor Cells

Figure 9:
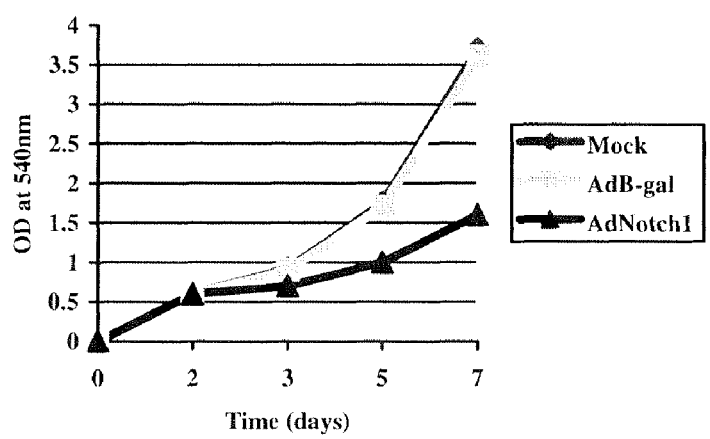
FIG. 9 shows the results of MTT proliferation assays on BON cells after infection with no virus (mock), β-gal and Notch1 adenoviruses, indicating that Notch1 infected BON cells had a proliferation rate 60% lower than the two control cells.

As noted above, the ability of Notch1 to suppress NE tumor growth has not been explored. We analyzed NE tumor cell growth after Notch1 induction. Cellular proliferation was analyzed by a calorimetric assay using 3-(4,5-dimethylthiazol-2-yl)-2,5-diphenyltetrazolium bromide (MTT) (Sigma). While proliferation rates of BON cells in the Mock-treated and B-gal adenovirus-infected group were identical over the 7-day period, Notch1-infected cells exhibited slower growth rates. At 7 days, Notch1-infected BON cells had a proliferation rate 60% lower than both control groups (FIG. 9). Similar growth suppression was seen after Notch1 induction in pulmonary H727 carcinoid cells and medullary thyroid cancer TT cells (not shown).

Example 7

Notch1 Induction Causes Cell Cycle Arrest in NE Tumor Cells

Notch1 overexpression has been shown to cause growth arrest in small cell lung cancer cell lines. (Radtke F, et al., Nature Reviews Cancer 2003; 3:756-767) The mechanism of this growth suppression has been shown to be G1 cell cycle arrest with an associated induction of the cell cycle inhibitor p21. Similarly, in hepatocellular cancer cells, Notch1 induction results in growth suppression which is at least partially mediated through a G1 cell cycle arrest. (Qi R Z, et al., Cancer Research 2003; 63:8323-8329)

1) Cell cycle analysis. For determination of cell cycle changes, BON, BON-Notch1, TT, TT-Notch1, H727, and H727-Notch1 cells are treated with VPA. The nuclei are harvested after 48 hours for propidium iodine staining and flow cytometry, and DNA synthesis is assessed by pulse treating BON, BON-Notch1, TT, TT-Notch1, H727, and H727-Notch1 cells with bromodeoxyuridine (BrdU). The harvested nuclei are stained with FITC-labeled anti-BrdU antibodies, and analyzed with propidium iodine and flow cytometry.

2) Expression of p21. In basal cell cancers, small cell lung cancers, and hepatocellular cancers, Notch1-mediated cell cycle arrest is associated with an increase in p21 expression. (Nicolas M, et al., Nature Genetics 2003; 33:416-421; Qi R Z, et al., Cancer Research 2003; 63:8323-8329; Sriuranpong V, et al., Cancer Research 2001; 61:3200-3205) In fact, Notch1 has been shown to bind with its partner CBF-1 to the p21 promoter leading to in increase in p21 gene transcription (Rangarajan A, et al., Embo Journal 2001; 20:3427-3436). In order to determine if Notch1 could be inducing expression of p21 in NE tumor cells, BON, BON-Notch1, TT, TT-Notch1, H727, and H727-Notch1 cells after treatment are analyzed for changes in p21 protein by Western blotting with commercially available antibodies.

Notch1 activation in BON, TT, and H727 cells are found to lead to cell cycle arrest due to upregulation of p21 protein and Notch1-mediated growth inhibition in NE tumor cells is predominantly due to cell cycle arrest through upregulation of p21.

Example 8

Suberic bishydroxamic Acid (SBHA) Inhibits Proliferation by Inducing Cell Cycle Arrest in Carcinoid Cancer Cells This example demonstrates the effects of suberic bishydroxamic acid (SBHA), a histone deacetylase inhibitor, and the most thoroughly clinically developed anti-cancer HDAC inhibitor to date (Kelly W K, Marks P A. Drug insight: Histone deacetylase inhibitors—development of the new targeted anticancer agent suberoylanilide hydroxamic acid. Nat Clin Pract Oncol. 2005 March;2(3):150-7) on the growth and neuroendocrine phenotype of carcinoid cancer cells and can be used for the treatment of patients with advanced carcinoid tumor disease. (SBHA) treatment of human gastrointestinal and pulmonary carcinoid cancer cells resulted in a dose-dependent inhibition of cell proliferation. Western blot analysis showed an increase in protein levels of p21 and p27, and a decrease in cyclin D1, indicating that the mechanism of this growth inhibition is cell cycle arrest. Furthermore, (SBHA) treatment suppressed two neuroendocrine tumor markers, chromogranin A and achaete-scute complex-like 1 (ASCL1). These (SBHA)-mediated changes in the growth and neuroendocrine phenotype of carcinoid cells were associated with activation of the Notch1 intracellular signaling cascade.

Materials and Methods

Cell Culture BON human GI carcinoid cancer cells, kindly provided by Drs. B. Mark Evers and Courtney M. Townsend, Jr. (University of Texas Medical Branch, Galveston, Tex., USA), and H727 human lung carcinoid cancer cells (American Type Tissue Collection, Manassas, Va., USA) were maintained as previously described (Sippel, R S et al., Raf-1 Activation Suppresses neuroendocrine marker and hormone levels in human gastrointestinal carcinoid cells. Am J Physiol Gastrointest Liver Physiol. 2003 August; 285(2):G245-54, Van Gompel J J et al., ZM336372, A Raf-1 Activator, Suppresses Growth and Neuroendocrine Hormone Levels in Carcinoid Tumor Cells. Mol Cancer Ther. 2005 June; 4(6):910-7)

Western Blot Analysis Carcinoid cancer cells were treated with SBHA for 48 hours and whole cell lysates were prepared as previously described (Sippel R S et al., Raf-1 Activation Suppresses Neuroendocrine Marker and Hormone Levels in Human Gastrointestinal Carcinoid Cells. Am J Physiol Gastrointest Liver Physiol. 2003 August; 285(2):G245-54). Total protein concentrations were quantified with a bicinchoninic acid assay kit (Pierce Biotechnology, Rockford, Ill., USA). Denatured cellular extracts were resolved by SDS-PAGE, transferred to nitrocellulose membranes (Schleicher and Schuell, Keene, N.H., USA), blocked in milk, and incubated with appropriate antibodies. The antibody dilutions were: 1:1,000 for Notch1 (Santa Cruz Biotechnology, Santa Cruz, Calif., USA), mammalian achaete-scute homolog 1 (ASCL1; BD Biosciences, San Diego, Calif., USA), chromogranin A (Zymed Laboratories, San Francisco, Calif., USA), and cyclin D1 (Cell Signaling Technology, Danvers, Mass., USA), 1:2,000 for p21 (Cell Signaling Technology) and p27 (Santa Cruz Biotechnology), and 1:10,000 for glyceraldehyde-3-phosphate dehydrogenase (G3PDH; Trevigen, Gaithersburg, Md., USA). Horseradish peroxidase conjugated goat anti-rabbit or goat anti-mouse secondary antibodies (Pierce Biotechnology) were used depending on the source of the primary antibody. For visualization of the protein signal, Immunstar (Bio-Rad Laboratories, Hercules, Calif., USA) or SuperSignal West Femto (Pierce Biotechnology) kits were used per the manufacturer's instructions.

Cell Proliferation Assay Carcinoid cancer cell proliferation was measured by the MTT (thiazolyl blue tetrazolium bromide; Sigma-Aldrich, St. Louis, Mo., USA) rapid calorimetric assay as previously described (Van Gompel J J et al., ZM336372, A Raf-1 Activator, Suppresses Growth and Neuroendocrine Hormone Levels in Carcinoid Tumor Cells. Mol Cancer Ther. 2005 June; 4(6):910-7). Briefly, cells were seeded in quadruplicate on 24-well plates and incubated for 24 hours to allow cell attachment. The cells were then treated with SBHA (Sigma-Aldrich) in concentrations of 0 to 50 μM and incubated for up to 6 days. The MTT assay was performed by replacing the standard medium with 250 μL of serum-free medium containing MTT (0.5 mg/mL) and incubated at 37° C. for 3 hours. After incubation, 750 μL of dimethyl sulfoxide (Sigma-Aldrich) was added to each well and mixed thoroughly. The plates were then measured at 540 nm using a spectrophotometer (μQuant; Bio-Tek Instruments, Winooski, Vt., USA).

Statistical Analysis Analysis of variance (ANOVA) with Bonferroni post hoc testing was performed using a statistical analysis software package (SPSS version 10.0, SPSS, Chicago, Ill.). A P-value of <0.05 was considered significant.

Results

SBHA Activates Notch1 Signaling in Carcinoid Cells

Figure 10:
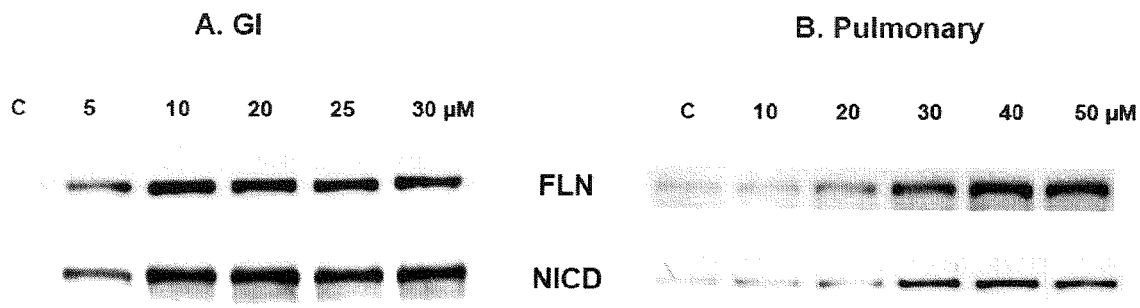
FIG. 10 shows that SBHA activates Notch1 in carcinoid cells. GI (A) and pulmonary (B) carcinoid cancer cells were treated with SBHA in the indicated concentrations for 48 hours and whole cell lysates were immunoblotted for Notch1. At baseline, Notch1 was absent or barely detectable in both cell lines. VPA treatment resulted in an increase in full-length Notch1 and the active Notch1 intracellular domain (NICD). G3PDH was used as a protein loading control.

To assess the ability of SBHA on to induce Notch1 expression in carcinoids, we performed Western blot analysis. At baseline, there was no or minimal Notch1 protein signal in untreated GI and pulmonary carcinoid cancer cells, respectively (FIG. 10). SBHA treatment of GI carcinoid cells in concentrations as low as 5 μM resulted in induction of both full-length Notch1 and the Notch1 intracellular domain (NICD), the active form of the protein (FIG. 10A). Significant Notch1 induction was not seen in pulmonary carcinoid cells until higher concentrations of SAHA, such as 20-30 μM, were administered (FIG. 10B).

Figure 11:
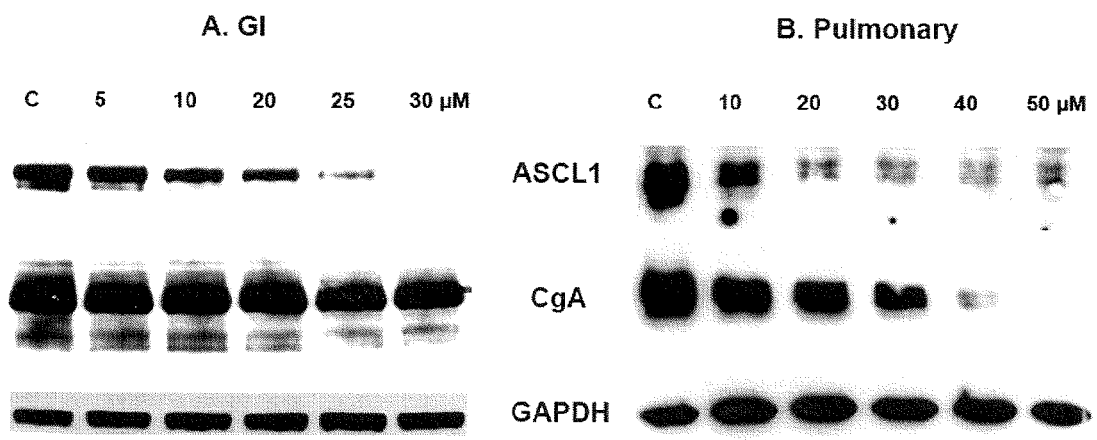
FIG. 11 shows that SBHA decreases levels of ASCL1 and chromogranin A in carcinoid cells. Treatment of GI (A) and pulmonary (B) carcinoid cells with SBHA for 48 hours resulted in a decrease in protein levels of the neuroendocrine tumor markers ASCL1 and chromogranin A (CgA).

SBHA-Mediated Notch1 Activation Results in Suppression of Neuroendocrine Tumor Markers Because overexpression of active Notch1 in GI carcinoid cells results in suppression of achaete-scute complex-like 1 (ASCL1), a basic helix-loop-helix transcription factor that regulates the neuroendocrine phenotype (Kunnimalaiyaan M, et al., Conservation of the Notch1 signaling pathway in gastrointestinal carcinoid cells. Am J Physiol Gastrointest Liver Physiol. 2005 October; 289(4):G636-42), Nakakura E K, et al., Regulation of neuroendocrine differentiation in gastrointestinal carcinoid tumor cells by notch signaling. J Clin Endocrinol Metab. 2005 July; 90(7):4350-6) a decrease in ASCL1 should result after Notch1 activation with SAHA. SAHA treatment of GI and pulmonary carcinoid cells resulted in a dose-dependent decrease in ASCL1 protein (FIG. 11). Treatment of GI carcinoid cells with 30 μM of the drug for 2 days suppressed ASLC1 to an undetectable level (FIG. 11A).

The impact of SAHA on expression of another neuroendocrine tumor marker, chromogranin A, was then examined. Chromogranin A is an acidic glycoprotein that is co-secreted with bioactive amines and peptides by carcinoids and other neuroendocrine tumors. Clinically, the presence of chromogranin A by immunohistochemistry can help confirm the histopathologic diagnosis of a neuroendocrine neoplasm, and serum chromogranin A levels are often monitored in patients as a metric of disease burden. As with ASCL1, SAHA treatment of carcinoid cancer cells suppressed levels of chromogranin A (FIG. 11). A dramatic decrease was seen in pulmonary carcinoid cells (FIG. 11B), with complete suppression after 2 day's treatment with 50 μM of SAHA. Compared to pulmonary carcinoid cells, the GI carcinoid cell line produces a relatively greater amount of chromogranin A at baseline, and only modest inhibition of chromogranin A was seen after 2 days of treatment (FIG. 11A). Taken together, the observed changes in ASCL1 and chromogranin A expression indicate that SAHA alters the neuroendocrine phenotype of carcinoid cancer cells.

SBHA Inhibits Carcinoid Cancer Cell Proliferation

Figure 12A:
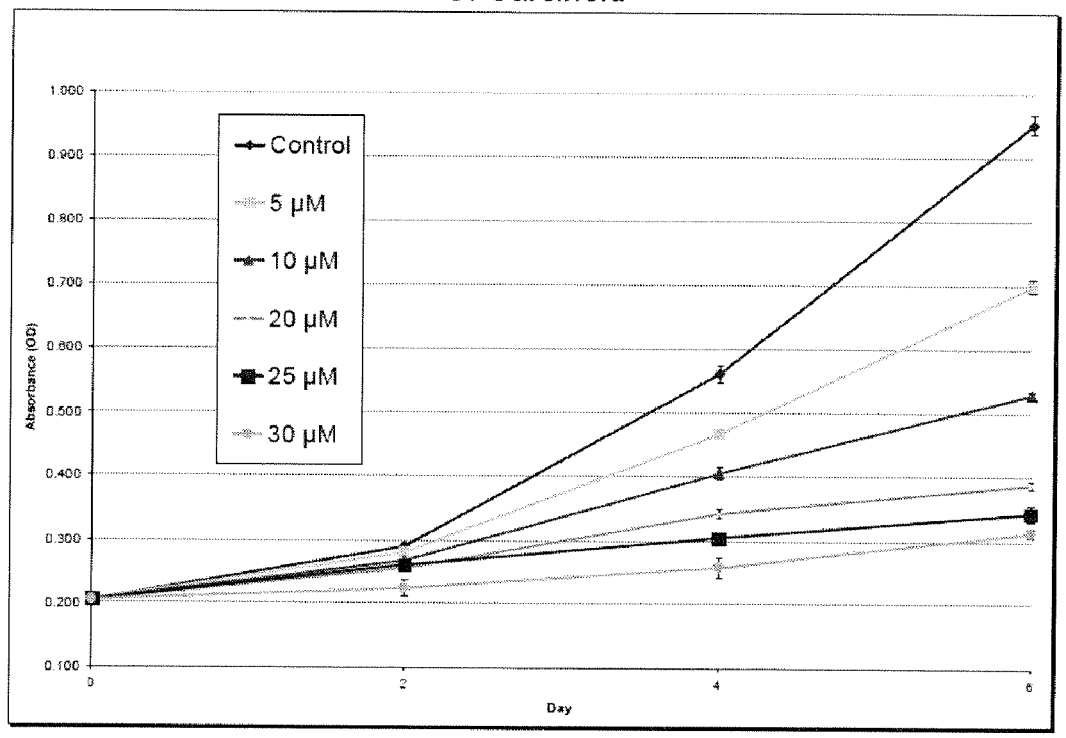
FIG. 12 shows that SBHA suppresses growth of carcinoid cancer cells in vitro. GI and pulmonary carcinoid tumor cells were treated with SBHA in the indicated concentrations for up to 6 days and cell viability was measured every 2 days with the MTT assay. SBHA inhibited cell proliferation in both GI (A) and pulmonary (B) carcinoid cell lines in a dose-dependent manner.
Figure 12B:
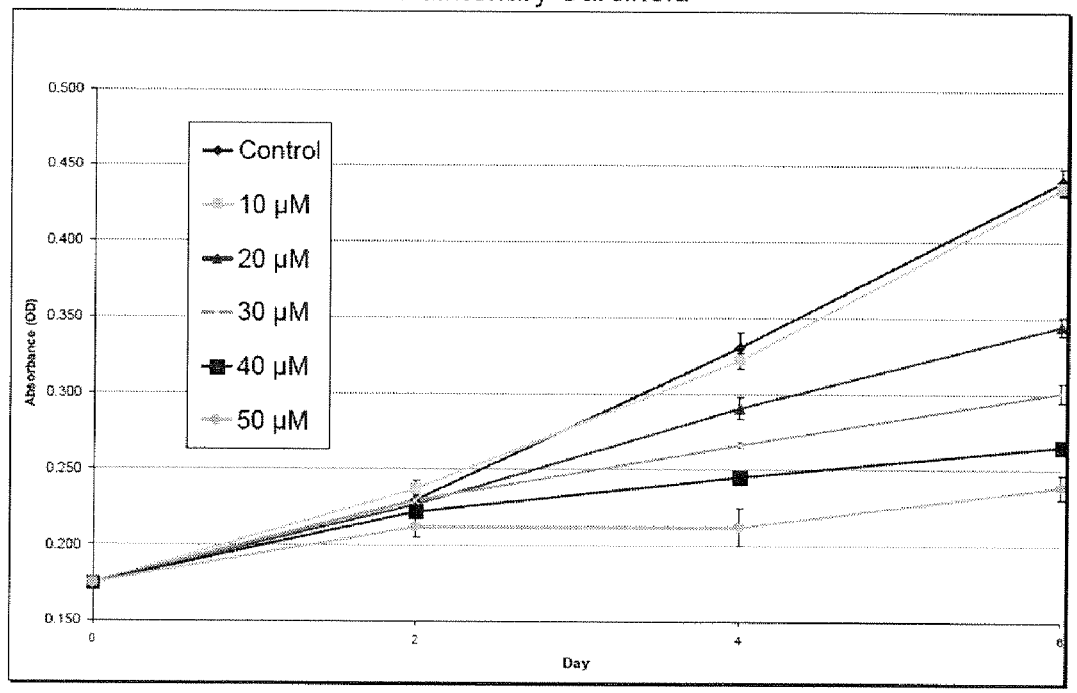

After confirming that SBHA activates Notch1 signaling and modifies the neuroendocrine phenotype in carcinoid cells, its effect on tumor cell growth was measured. GI carcinoid cells treated with SBHA exhibited a profound dose-dependent inhibition of cell proliferation (FIG. 12A). Significant growth inhibition was seen after 4 days of exposure to 5 μM of SBHA. SBHA treatment of pulmonary carcinoid cells also resulted in dose-dependent growth suppression, although higher concentrations of the drug were required (FIG. 12B). Interestingly, the concentrations of SBHA that produced growth inhibition, 20-50 μM, were the same concentrations that yielded Notch1 induction as observed by Western blot (FIG. 10B).

Figure 13A:
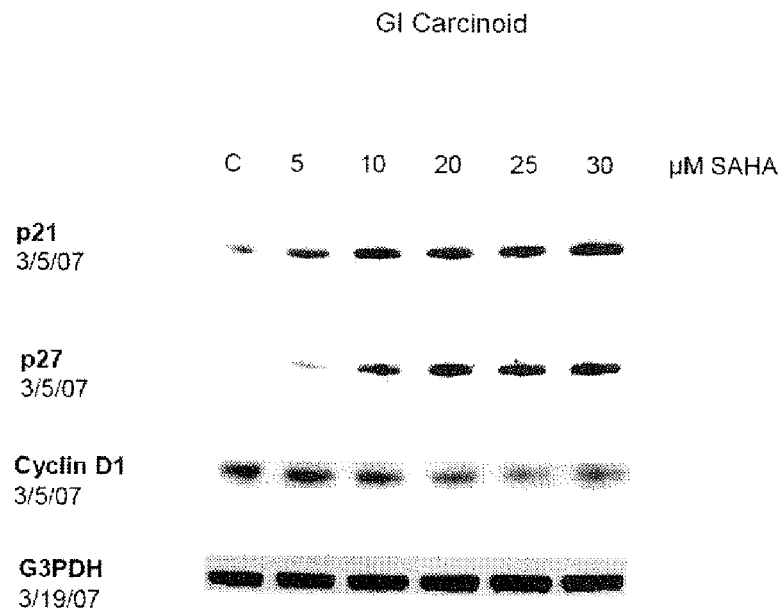
FIG. 13 shows that SBHA-mediated carcinoid growth inhibition is due to cell cycle arrest. GI (A) and pulmonary (B) carcinoid cells were treated with SBHA for 48 hours and immunoblotting was performed to measure levels of cell cycle proteins. SBHA induced expression of cyclin-dependent kinases p21 and p27, and downregulated cyclin D1, indicating cell cycle arrest.
Figure 13B:
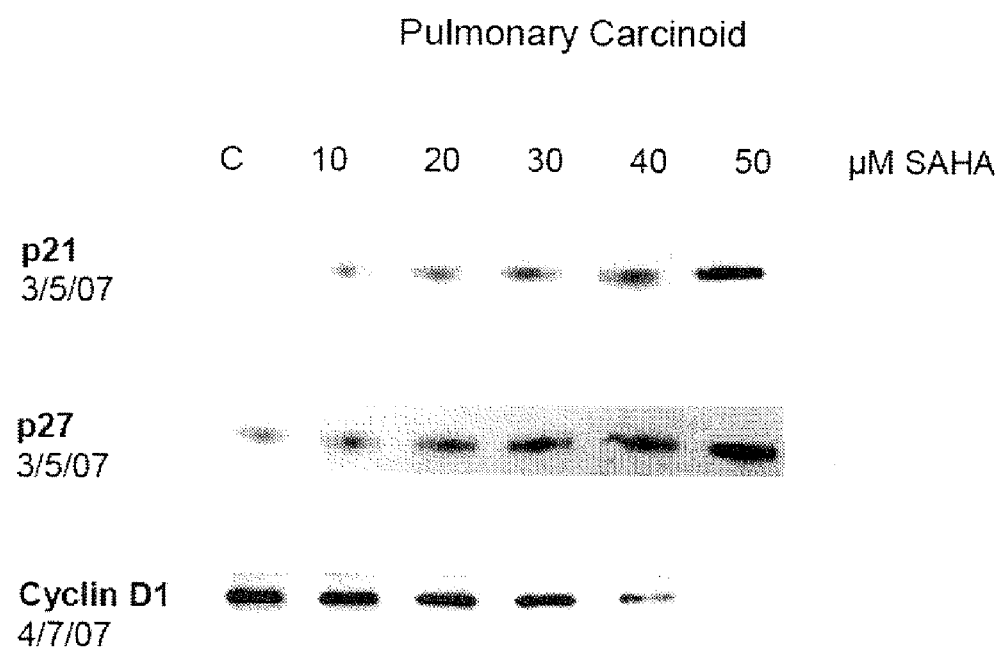

Furthermore, Western blot analysis demonstrated that SBHA increased levels of the cyclin-dependent kinase inhibitors p21 and p27, and decreased levels of the cell cycle promoter, cyclin D1, in both GI and pulmonary carcinoid tumor cells (FIG. 13). While not willing to be bound by any speculation on the of action for this effect, the above results suggest that the growth inhibition induced by SBHA is mediated by cell cycle arrest. This is because previous research has shown that activation of Notch1 in neuroendocrine tumor cell lines such as small cell lung cancer (Sriuranpong V et al., Notch signaling induces rapid degradation of achaete-scute homolog 1. Mol Cell Biol. 2002 May; 22(9):3129-39) and medullary thyroid cancer (Kunnimalaiyaan M et al., Overexpression of the NOTCH1 intracellular domain inhibits cell proliferation and alters the neuroendocrine phenotype of medullary thyroid cancer cells. J Biol Chem. 2006 Dec. 29; 281(52):39819-30) leads to cell cycle arrest. Progression through the cell cycle is controlled by cyclindependent kinases (CDKs), which are regulated by cyclins and CDK-inhibitors (Baradari V et al., Antiproliferative and proapoptotic effects of histone deacetylase inhibitors on gastrointestinal neuroendocrine tumor cells. Endocr Relat Cancer. 2006 December; 13(4):1237-50). GI phase cell cycle arrest is associated with increases in the Cip/Kip family CDK-inhibitors p21 and p27, and degradation of cyclin D1, which results in downregulation of CDK4.

The above results are the first to demonstrate that Notch1 signaling can be activated in carcinoid tumors in vivo, even though Notch1 signaling was known to be minimal or absent in neuroendocrine tumors such as small cell lung cancer (Sriuranpong V et al., Notch signaling induces cell cycle arrest in small cell lung cancer cells. Cancer Res. 2001 Apr. 1; 61(7):3200-5, Sriuranpong V et al., Notch signaling induces rapid degradation of achaete-scute homolog 1. Mol Cell Biol. 2002 May; 22(9):3129-39), medullary thyroid cancer (Kunnimalaiyaan M. et al., Overexpression of NOTCH1 intracellular domain inhibits cell proliferation and alters the neuroendocrine phenotype of medullary thyroid cancer cells. J Biol Chem. 2006 Dec. 29; 281 (52):39819-30), and carcinoid tumors (Kunnimalaiyaan M et al., Conservation of the Notch1 signaling pathway in gastrointestinal carcinoid cells. Am J Physiol Gastrointest Liver Physiol. 2005 October; 289 (4):G636-42, Kunnimalaiyaan M et al., enhancer of split-1 (HES-1), a Notch1 effector, inhibits the growth of carcinoid tumor cells. Surgery. 2005 December; 138(6):1137,42; discussion 1142, Nakakura E K et al., Regulation of neuroendocrine differentiation in gastrointestinal carcinoid tumor cells by notch signaling. J Clin Endocrinol Metab. 2005 July; 90(7):4350-6) and Notch1 overexpression in carcinoid and medullary thyroid cancer cell lines resulted in inhibition of cell growth and suppression of neuroendocrine tumor markers and hormones (Kunnimalaiyaan M, et al. Conservation of the Notch1 signaling pathway in gastrointestinal carcinoid cells. Am J Physiol Gastrointest Liver Physiol. 2005 October; 289(4):G636-42, Knupfer M M, Hernaiz-Driever P, Poppenborg H, et al. Valproic acid inhibits proliferation and changes expression of CD44 and CD56 of malignant glioma cells in vitro. Anticancer Res 1998; 18:3585-3589). Similarly, Baradari et al. showed that treatment of carcinoid tumor cells with other HDAC inhibitors, including sodium butyrate and trichostatin A, led to an increase in p21 and p27, and a concomitant downregulation of cyclin D1, indicating the induction of cell cycle arrest (Baradari V, Huether A, Hopfner M, Schuppan D, Scherubl H. Antiproliferative and proapoptotic effects of histone deacetylase inhibitors on gastrointestinal neuroendocrine tumor cells. Endocr Relat Cancer. 2006 December; 13(4): 1237-50).

Of all the HDAC inhibitors, SBHA has undergone the most extensive clinical development as an antineoplastic agent. SBHA causes growth arrest and death in numerous malignant cell lines at concentrations that have minimal toxic effects in normal cells (20). Currently, several clinical trials are underway evaluating the efficacy of SBHA alone or in combination with other agents in the treatment of a variety of hematologic and solid tumors, including carcinoma of the colon and rectum, breast, lung, kidney, and prostate gland (ClinicalTrials.gov website: Clinical trials of SAHA for cancer. [cited Apr. 18, 2007]. Available from: http://clinicaltrials.gov/ct/search?term=saha+cancer&submit=Search). In October of 2006, the United States Food and Drug Administration approved the use of SAHA, which has the generic drug name of vorinostat, for the treatment of cutaneous T-cell lymphoma (National Cancer Institute website: FDA approval for vorinostate. [cited Apr. 18, 2007]. Available from: http://www.cancer.gov/cancertopics/druginfo/fda-vorinostat). As phase I clinical trials have established the safety profile of the drug, the data above suggest that SAHA represents a promising new potential therapy for patients with advanced carcinoid cancer, a disease for which few effective treatments currently exist.

Example 9

SBHA Activates Notch1 Signaling and Induces Apoptosis in Medullary Thyroid Cancer Cells Human MTC TT cells were treated with SBHA in concentrations up to 25 µM and analyzed by Western blotting for evidence of Notch1 pathway activation and changes in neuroendocrine markers. MTT assay was used to measure cell viability. Finally mechanism of growth inhibition was analyzed by Western blotting.

Results: At baseline, no active Notch1 protein was present in MTC cells. Treatment with SBHA resulted in a dose-dependent induction of the active form of Notch1, and a concomitant decrease in ASCL1, a downstream target of Notch1 signaling, as well as the neuroendocrine tumor marker chromogranin A. SBHA treatment resulted in a dose-dependant decrease in cell viability. SBHA-treated cells had an increase in protein levels of cleaved poly ADP-ribose polymerase (PARP) and caspase-3, indicating that the growth inhibition was mediated by apoptosis.

Conclusion: SBHA activates Notch1 signaling, suppresses production of neuroendocrine tumor markers, and inhibits proliferation in MTC cells. The mechanism of growth suppression caused by SBHA is apoptosis. Therefore, SBHA is a potential new treatment for patients with advanced MTC.

Example 10

Notch1 Inhibits the Hedgehog Signaling Pathway in NE Tumor Cells

As previously mentioned, Notch1 acts as a tumor suppressor in the skin, in part, by inhibition of the Hedgehog signaling pathway (Nicolas M, et al., Nature Genetics 2003; 33:416-421). Several investigators have reported that the uncontrolled activation of the Hedgehog signaling pathway results in cancers of the brain, muscle, skin, lung, and GI tract. (Berman D M, et al., Nature 2003; 425:846-851; di Magliano M P, et al., Nature Reviews Cancer 2003; 3:903-911; Karhadkar S S, et al., Journal of Urology 2003; 169:162) In these studies, increased levels of Hedgehog signaling appear to be both sufficient to initiate cancer formation and required for tumor survival. In small cell lung cancer, a NE tumor of the lung, the hedgehog signaling pathway is activated. (Watkins D N, et al., Nature 2003; 422:313-317) As shown in the preliminary results (section C.10), we found that the Hedgehog pathway is activated in BON, H727, and TT cells. The results below show that the Notch1-mediated growth suppression in human NE tumors is due to inhibition of the Hedgehog signaling pathway.

1) The Hedgehog signaling pathway. Members of the hedgehog signaling pathway include sonic hedgehog (Shh) (a hedgehog pathway ligand), patched (PTC) (a hedgehog pathway receptor), and the Gli proteins (downstream transcriptional targets of Shh). (Watkins D N, et al., Nature 2003; 422:313-317)

We found that BON, H727, and TT cells express relatively high levels of Shh, PTC1, Gli1, Gli2, and Gli3 by real-time PCR.

Figure 14:
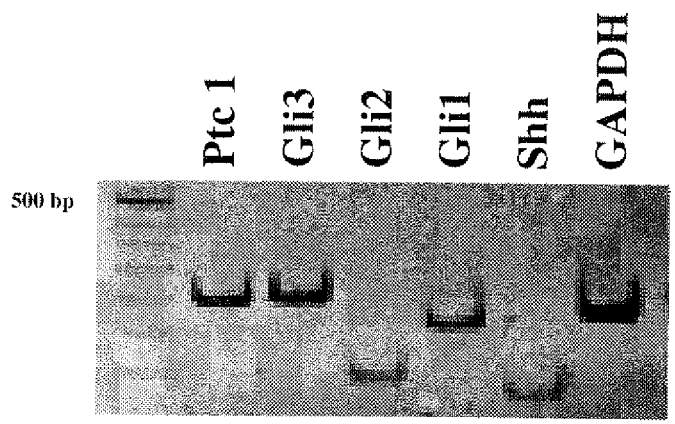
FIG. 14 shows RT-PCR amplification results of BON cell mRNA for the listed members of the hedgehog pathway.
Figure 15:
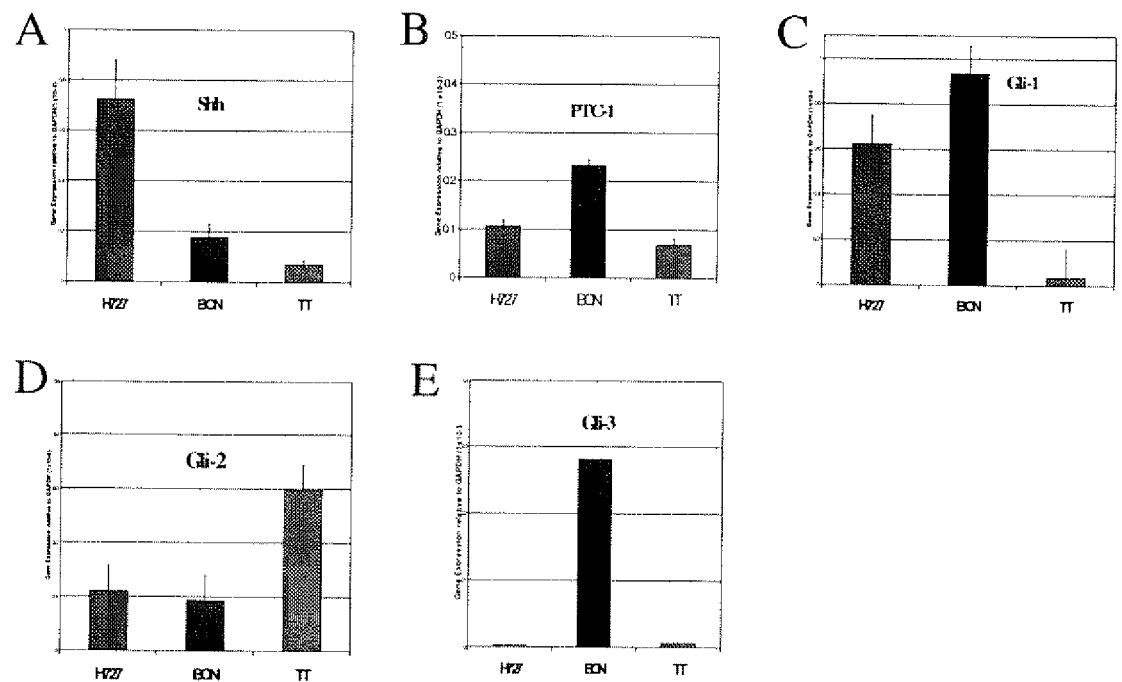
FIG. 15 shows results of real-time RT-PCR performed on mRNA extracted from pulmonary carcinoid H727 cells, pancreatic carcinoid BON cells, and medullary cancer TT cells for (A) Shh, (B) PTC1, (C) Gli1, (D) Gli2, and (E) Gli3. The values are relative to GAPDH expression.
Figure 16:
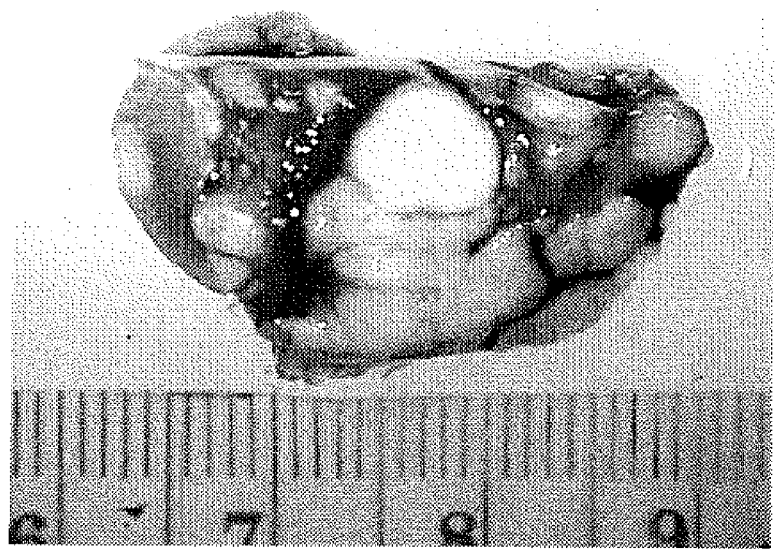
FIG. 16 shows Mouse liver 12 weeks after intrasplenic injection of TT cells. Note multiple white metastatic lesions.
Figure 17:
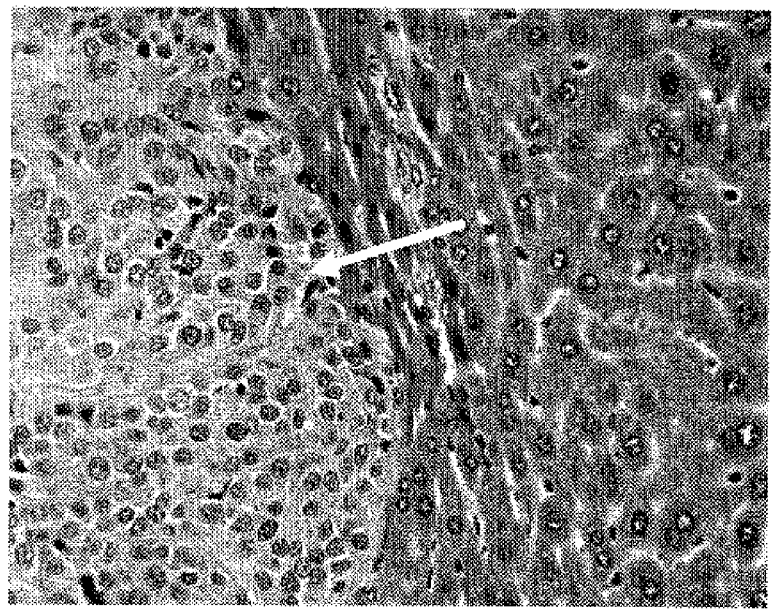
FIG. 17 shows Histologic section of nude mice NE liver metastases.
Figure 18:
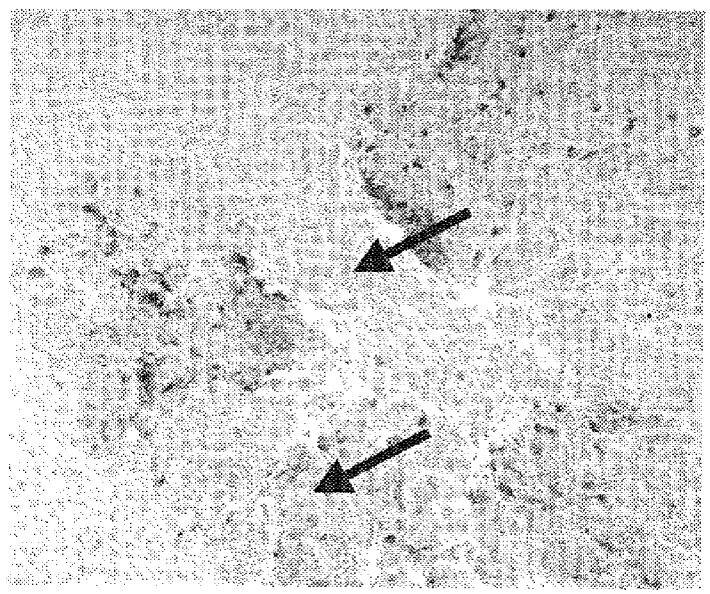
FIG. 18 shows Calcitonin immunohisto-chemistry on nude mice medullary thyroid cancer liver lesions
Figure 19:
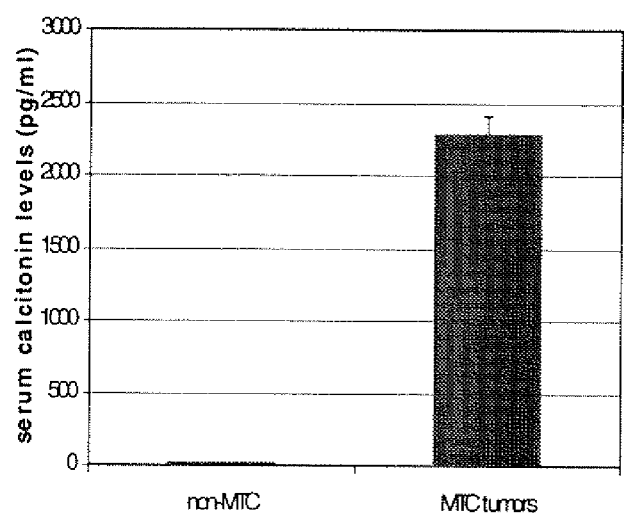
FIG. 19 shows Serum calcitonin levels on mice without and with medullary thyroid cancer tumors.

We initially confirmed the presence of mRNAs for various hedgehog pathway members including Shh, PTC1, Gli1, Gli2, and Gli3 in human NE tumor cell lines (FIG. 14). To quantify the levels of message, we utilized real-time PCR protocols developed by the Bushman lab33. We found that BON, H727, and TT cells express relatively high levels of Shh, PTC1, Gli1, Gli2, and Gli3 (FIG. 15).

2) The Effect of Notch1 on Hedgehog signaling. BON, TT, and H727 cells are treated with varying dosages of VPA. Total RNAs are be harvested and purified as previously described. (Sippel R S, et al., Am J Physiol Gastrointest Liver Physiol 2003; 285:G245-G254) Reverse transcription and real time PCR are used as described above. Briefly, real-time PCR is performed in an iCycler iQ Real-Time PCR Detection System (Bio-Rad, Hercules, Calif.) in a 96 well plate. For each reaction, 1.5 µl cDNA are added to a SYBR Green PCR master mix (Applied Biosystems, Foster City, Calif.) along with primers. Final primer concentrations are 300 nM except for Gli1 antisense primer (900 nM). Amplification is performed with an initial denaturation step of 10 min at 95° C., followed by 50 cycles of denaturation at 95° C. for 15 sec and primer annealing/extension at 60° C. for 1 min. All reactions are run in duplicate. Relative gene expression of each target is determined by normalizing the expression to GAPDH by comparative $C_T$ method using the following formula: $2^{-\Delta\Delta C_T}$ where $^{\Delta C}T$ is the difference in threshold cycles for target and reference (Applied Biosystems, Foster City, Calif.). For size verification of amplified products, 8 µl of each BON reaction is run on a 10% non-denaturing acrylamide gel and visualized by EtBr staining.

Notch1 activation in BON, TT, and H727 cells results in decreased levels of Shh, PTC1, Gli1, Gli2 and Gli3 protein. The degree of reduction varies between cell lines because BON, TT, and H727 cells have slightly different basal levels of each of the factors. Thus, each particular tumor may utilize different components of the pathway.

Example 11

Inhibition of Hash1, Shh, PTC1, Gli1, Gli2, and/or Gli3 Level or Function for Treating NE Tumors As described above, the expression level of Hash1, or of a gene that codes for a member of the Hedgehog signaling pathway, such as Shh, PTC 1, Gli1, Gli2, and/or Gli3 may be inhibited using suitable antisense nucleic acid molecules, or corresponding small interfering RNA molecules. Alternatively, antibodies, preferably humanized antibodies against Hash1 protein, or Shh, PTC1, Gli1, Gli2, and/or Gli3, may be administered to the patient in need thereof for the treatment NE tumors.

Example 12

Down Regulation of Hash1 Decreases in NE Marker and Hormone Production

There are data suggesting that hASH1 is required for the development of NE cells. In transgenic knockout mice for mammalian achaete-scute homolog-1 (mASH1), the murine homolog of hASH1, homozygous mice progeny die at birth with a lack of NE cells in the lung, thyroid, and GI tract. (Borges M, et al., Nature 1997; 386:852-855) Furthermore, in small cell lung cancer cells, we have shown that loss of hASH1 by treatment with hASH1 anti-sense oligonucleotides resulted in a significant decrease in NE markers in vitro. (Borges M, et al., Nature 1997; 386:852-855) However, the role of hASH1 in mediating the NE phenotype in GI and thyroid NE cells is not known.

1) hASH1 anti-sense oliaonucleotides. hASH1 anti-sense oligonucleotides are used to determine if hASH1 is required for NE marker and hormone expression in human carcinoid cells. A hASH1 anti-sense oligonucleotide c5p1476, 5'-GGAGCCCACUGCUUU-3' (SEQ ID NO: 1), directed at the hASH1 3'UTR is a very potent inhibitor of hASH1 expression in small cell lung cancer cells. (Borges M, et al., Nature 1997; 386:852-855) Another hASH1 anti-sense oligonucleotide c5p25, 5'-UCCUACUAAGGCUGC-3' (SEQ ID NO: 2), has minimal hASH1 inhibitory activity while 2 missense oligonucleotides c5pMiss1, 5'-GCUACAUCUGGUCGC-3' (SEQ ID NO: 3) and c5pMiss2, 5'-CACUGAUGCAC-CUGU-3' (SEQ ID NO: 4), have no affect on hASH1 expression in small cell lung cancer cells. (Borges M, et al., Nature 1997; 386:852-855) These sequences are used for the following studies.

2) Cell lines. BON, H727, and TT cells express high levels of hASH1 and chromogranin A. As a control, non-NE, pancreatic adenocarcinoma cell lines MIA and BXPC3, which lack hASH1 and chromogranin A by Western analysis are used. (See FIG. 6)

3) Oligonucleotide treatment. 100 nM phosphorothioate oligodeoxynculeotides with C-6 propyne modifications at dC and dU are reconstituted with 2.5 µg/ml of GS2888 cytofectin (Gilead Sciences) in OptiMEM (GIBCO) media. The above cell lines are exposed to each of the oligonucleotides and cytofectin alone. Cellular extracts and supernatant are harvested at 24, 48, and 72 hours.

4) hASH1 and NE marker expression. Cellular extracts are analyzed using western blots with hASH1, chromogranin A, synaptophysin, and neuron-specific enolase, and serotonin and calcitonin secretion are assessed using an ELISA assay, as described previously.

Treatment with hASH1 anti-sense oligonucleotides results in a decrease in NE marker expression and serotonin secretion.

Example 13

Induction of HES-1 Suppresses Hormone Production From NE Tumor Cells

It is known that in small cell lung cancer cells that overexpression of HES-1 can dramatically reduce levels of iASHI steady-state mRNA. The following experiments show that down-regulation of hASH1 and NE markers can be induced solely by HES-1 over-expression.

1) Inducible HES-1 constructs. A 1.7 kb fragment containing the HES-1 coding region was cloned into the tetracycline-inducible vector TRE creating TRE-HES-1. The addition of tetracycline (1 µg/ml) causes significant induction of the HES-1 gene, and high levels of inducible-HES-1 protein were achieved utilizing this technique.

2) Creation of BON-HES-1, TT-HES-1, and H727-HES-1 cells. BON-TET, TT-TET, and H727-TET cells re transfected with TRE-HES-1 and resistant cells selected. The resulting BON-HES-1, TT-HES-1, or H727-HES-1 cells are then tested for tetracycline-inducible HES-1 expression by treatment with tetracycline (1 µg/ml) and Western analysis for HES-1 as detailed above.

3) NE marker and hormone production. After confirming inducibility of HES-1 in these cells, cellular extracts are analyzed using western blots with hASH1, chromogranin A, synaptophysin, and neuron-specific enolase, and serotonin and calcitonin secretion are assessed using ELISA assays, as described above.

HES-1 overexpression causes a reduction in hASH1 and NE marker expression.

Example 14

Notch1-Mediated Hormone Suppression DA1epends on the MAP Kinase Pathway

There is some evidence to suggest that Notch1 may be signaling through a MAPK-dependent pathway. Notch1-mediated growth arrest in small cell lung cancer cell lines is partially dependent on MAP kinase phosphorylation. (Sriuranpong V, et al., Cancer Research 2001; 61:3200-3205) Furthermore, Notch1 signaling in breast cancer cell lines has been shown to require the ras pathway. (Fitzgerald K, et al., Oncogene 2000; 19:4191-4198) We have illustrated that both activation of the Notch1 and the raf-1/MEK/MAPK pathways reduce hormone production in NE tumors. Furthermore, we demonstrated that induction of Notch1 in NE tumor cells lead to activation of the MAPK pathway. This example illustrates that Notch1-mediated hormone suppression in NE tumor cells is dependent on induction of the MAPK pathway.

1) MEK inhibitors. BON, BON-Notch1, H727, H727-Notch1, TT, and TT-Notch1 cells are pre-treated with either PD098059 (25-50 uM) or U0126 (5-20 uM) (both well-characterized MEK inhibitors) (Sippel R S, et al., Am J Physiol Gastrointest Liver Physiol 2003; 285:G245-G254; Sippel R S, et al., Surgery 2003; 134:866-871), alone or in combination, followed by addition of control or doxycycline (1 µg) for 24, 48, and 96 hours. Cells are then analyzed with the following methods.

2) Confirmation of MEK inhibition. To confirm MEK inhibition after treatment with PD098059 and U0126, cellular extracts are analyzed by Western blots utilizing antibodies against MEK, phospho-MEK, ERK1/2, and phospho-ERK1/2. MAPK in vitro kinase assay with a commercially available kit (Cell Signal Technology) is used to confirm blockade of MEK activity.

3) hASH1 and NE marker expression. To determine if MEK inhibition blocks Notch1-mediated NE marker suppression, cellular extracts are analyzed using western blots with hASH1, chromogranin A, synaptophysin, and neuron-specific enolase, and serotonin or calcionin secretion will be assessed using an ELISA assay, as described above.

PD098059 and U0126 block Notch1-mediated hormone suppression.

Example 15

Notch1 Inhibits NE Tumor Proliferation and Hormone Production In Vivo

A mouse model of NE tumor progression and liver metastasis has been developed utilizing nude mice and intrasplenic injection of human NE tumor cells.

GI carcinoid BON, pulmonary carcinoid H727, or medullary thyroid cancer TT cells were injected into the spleens of the nude mice. By 6-8 weeks, the murine livers harbored NE tumor liver metastases (see FIGS. 16-19). The experiments in this example shows that activation of Notch1 inhibits tumor growth and reduces hormone production by NE tumors in vivo.

1) Animal care. All animal studies are performed in accordance with the University of Wisconsin Animal Care Committee. Nude (nu/nu) mice (weighing about 20 g and at 4-5 weeks of age) undergo surgery in an isolation hood. Anesthesia consists of inhalational halothane. BON, BON-Notch1, TT, TT-Notch1, H727, and H727-Notch1 cells ($10^7$) are injected into the spleen 100-200 µl with a 25 g needle). Animals recover under a heat lamp and constant monitoring in their cages until fully awake and mobile. Any animal that appears to be suffering undue pain is euthanized. Mice are then sacrificed at various time intervals depending on the model.

2) Surgery. For each experiment, nude mice are divided into 4 groups as listed in Table 1. Based on preliminary results, in order to detect a >30% reduction in tumor size in the treatment group with a power of 80%, 52 animals are used in each group (total=208).

With a left subcostal incision, the spleen is identified and 2 surgical clips are placed across the mid-portion, creating 2 hemispleens. BON or BON-Notch1 cells ($10^7$) are then injected into the distal hemispleen. One minute later, the animals undergo a distal splenectomy, resecting the injection site. In order to activate Notch1 in the injected BON-Notch1 cells, the mice are treated with doxycycline. At the time of tumor cell injection, the mice are also treated with control or doxycycline by intraperitoneal injection twice weekly. While the majority of animals are sacrificed at 15 weeks after surgery, 3 animals from each group are sacrificed at 3 weeks intervals to fully assess tumor burden by gross and histologic examination of the liver.

3) Notch1 activation and NE hormone production. Notch1 activation effects in vivo on NE hormone production by the tumor cells are determined. The liver lesions from animals sacrificed at 3 weeks intervals are microdissected from normal liver and the protein extracted. Western analysis on these tumor cell extracts with Notch1, HES-1, and hASH1 antibodies is performed to confirm Notch1 pathway activation. The effects of Notch1 induction on NE hormone production are determined using Western analysis on the microdissected tumors with chromogranin A antibody. Serotonin or calcitonin ELISAs are also utilized to determine these NE marker levels.

4) Serum serotonin or calcitonin levels. Mice with carcinoid or MTC liver metastases are known to have markedly elevated serum serotonin or calcitonin levels by ELISA, respectively. Serum serotonin or calcitonin levels are determined in each individual mouse at 3-week intervals after NE tumor cell injection by ELISA, allowing longitudinal follow up on hormone production in each individual animal. Any changes in serum serotonin or calcitonin levels could be due to either alterations in tumor burden or differentiation.

Figure 20:
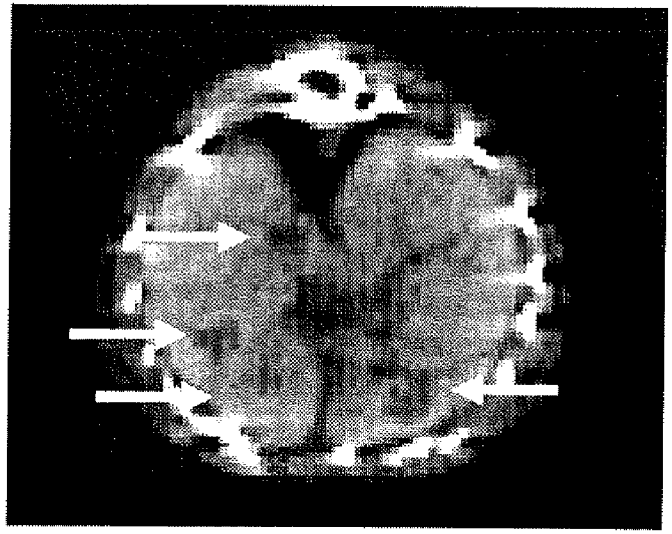
FIG. 20 shows Cross-sectional microCT scan on a mouse after intrasplenic injection of tumor cells. Note numerous metastases with in the liver (arrows).
Figure 21:
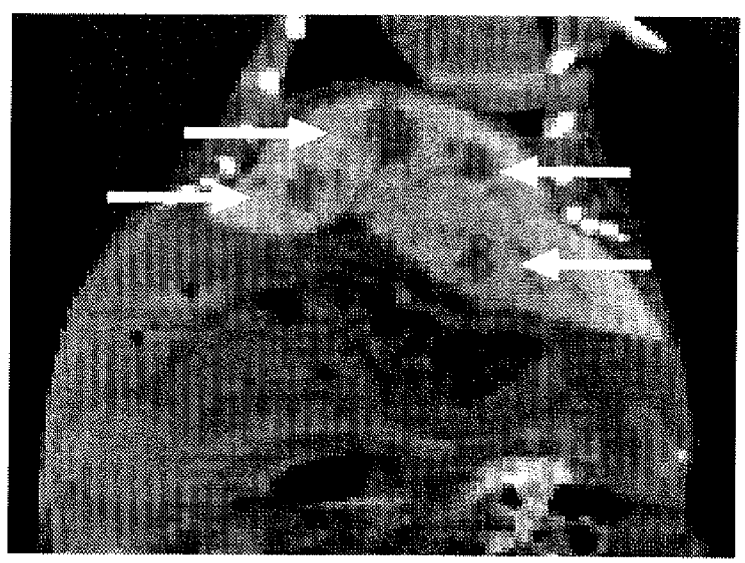
FIG. 21 shows MicroCT scan (coronal view) on a mouse after intrasplenic injection of tumor cells. Note numerous metastases with in the liver (arrows).

5) Assessing tumor burden. In order to determine the tumor burden in each individual animal, each mouse undergoes a body micro-computed tomography (microCT) scan. Hepatic metastatic lesions have been successfully and reproducibly imaged after intrasplenic injection of tumor cells in mice (FIGS. 20 and 21).

After intrasplenic injection of NE tumor (BON, TT, or H727) cells, mice are subjected to scanning on a microCT scanner (ImTek). Each animal is anesthetized during the scanning procedure (8-12 min). The animals receive an injection of ITG, a polyiodinated triglyceride formulated into a chylomicron remnant-like delivery vehicle that specifically targets hepatocytes. The agent selectively accumulates in hepatocytes prior to undergoing metabolism and biliary excretion. The agent is given i.v. via tail vein injection. Typical injection volumes are around 200 µl for a 20 gram mouse. Tumor volumes are calculated and compared to normal liver volume using image analysis software routinely utilized. Preliminary studies in several mouse models indicate that this technique can accurately detect mouse liver lesions less than 300 microns in diameter (Weichert J P, et al., J Med Chem 1995; 38:636-646; Weichert J P, et al., Radiology 2000; 216: 865-871).

6) Timing of doxycycline treatment. Whether Notch1 overexpression causeS regression of established primary and metastatic lesions are tested by treating the mice with doxycycline after tumor development.

Example 16

Hedgehog Signaling Blockade Inhibits NE Tumor Regression In Vivo

The following experiments show that blockade of Hedgehog signaling inhibits NE tumor progression in vivo.

1) Cyclopamine and animals. Cyclopamine has been shown to be a specific inhibitor of the Hedgehog pathway (di Magliano M P, et al., Nature Reviews Cancer 2003; 3:903-911; Berman D M, et al., Science 2002; 297:1559-1561), and has been utilized in several murine models (Berman D M, et al., Nature 2003; 425:846-851; Thayer S P, et al., Nature 2003; 425:851-856; Lamm M L G, et al., Developmental Biology 2002; 249:349-366). In these studies, cyclopamide completely blocked Hedgehog signaling with no adverse side effects to the mice, and caused regression of tumors dependent on Hedgehog signaling. (Berman D M, et al., Nature 2003; 425:846-851; Berman D M, et al., Science 2002; 297: 1559-1561)

Sixty nude mice undergo intrasplenic injection of NE tumor cells as described above. Six weeks after NE tumor cell injection, the animals begin treatment with cyclopamine (n=30) or control (n=30) by daily intraperitoneal injection (50 mg/kg/d). Intraperitoneal injection of cyclopamine in mice has been shown to result in complete blockade of Hedgehog signaling in mice with no adverse effects. Treatment continues for 8 weeks.

2) Interval assessment of tumor burden. All animals undergo microCT scanning every week for 8 weeks as described above. Blood is sampled weekly for measurement of serotonin or calcitonin levels.

3) Measurement of Hedgehog signaling inhibition. Cycopamine is confirmed to inhibit Hedgehog signaling within the NE tumor cells. The liver lesions from animals sacrificed at 2 weeks intervals (n=3 per group) are microdissected from normal liver and total RNA extracted. Tumors in cycloamine treated mice are analyzed for downregulation of Gli1 expression by real-time PCR when compared to control animals.

Cyclopamine treatment is found to cause in vivo NE tumor growth inhibition and possible regression.

Example 17

Valproic Acid Activates Notch1 Signaling and Regulates the Neuroendocrine Phenotype in Carcinoid Cancer Cells Valproic acid (VPA) is a branched-chain fatty acid that has long been used for the treatment of patients with epilepsy and other neuropsychiatric disorders (Henry, T R., The History of Valproate in Clinical Neuroscience. Psychopharmacol Bull 2003; 37 Suppl 2:5-16). In addition to other properties, VPA is a well-established histone deacetylase (HDAC) inhibitor and is currently in clinical trials for various cancers. Stockhausen and colleagues recently described the ability of VPA to increase Notch1 protein levels in neuroblastoma cells (Stockhausen, M T et al., Effects of the Histone Deacetylase Inhibitor Valproic Acid on Notch Signalling in Human Neuroblastoma Cells. Br J Cancer 2005; 92:751-759).

In this example we describe the effects of VPA on human gastrointestinal and pulmonary carcinoid tumor cell lines. VPA treatment resulted in a dose-dependent inhibition of carcinoid cell growth in vitro. Western blot analysis and flow cytometry demonstrated that this growth inhibition is mediated by cell cycle arrest at the GI phase. Besides inhibiting cancer cell growth, VPA also suppressed production of the neuroendocrine tumor marker chromogranin A (CgA). These effects of VPA on carcinoid cell growth and CgA production were associated with Notch1 signaling activation by an increase in protein levels of both full-length Notch1 and the active Notch1 intracellular domain (NICD). Luciferase reporter assays confirmed that the Notch1 induced by VPA binds with CBF1 and the achaete-scute complex like 1 (ASCL1) promoter repressor, indicating that it is functionally active. Small-interfering RNA (siRNA) against Notch1 countered the effects of VPA on carcinoid cell growth and neuroendocrine marker production, providing further evidence that VPA acts through Notch1. Finally, VPA inhibited carcinoid tumor growth in vivo in a xenograft model. These findings demonstrate that VPA has anti-tumor effects in carcinoid cells in vitro and in vivo, and suggest that these effects are mediated by activation of Notch1 signaling. A clinical trial of VPA for patients with advanced carcinoid cancer are conducted based on the above.

Materials and Methods

Cell Culture BON human gastrointestinal (GI) carcinoid tumor cells, kindly provided by Drs. B. Mark Evers and Courtney M. Townsend, Jr. (University of Texas Medical Branch, Galveston, Tex.), and NCI-H727 human pulmonary carcinoid tumor cells (American Type Culture Collection, Manassas, Va.) were maintained as previously described (Sippel, R S et al., Raf-1 Activation Suppresses Neuroendocrine Marker and Hormone Levels in Human Gastrointestinal Carcinoid Cells. Am J Physiol Gastrointest Liver Physiol 2003; 285:G245-254, Van Gompel J J et al., ZM336372, A Raf-1 Activator, Suppresses Growth and Neuroendocrine Hormone Levels in Carcinoid Tumor Cells. Mol Cancer Ther 2005; 4:910-917).

Cell Proliferation Assay Carcinoid tumor cell proliferation was measured by the MTT (methylthiazolyldiphenyl-tetrazolium bromide; Sigma-Aldrich, St. Louis, Mo.) rapid colorimetric assay as previously described (Van Gompel J J et al., ZM336372, A Raf-1 Activator, Suppresses Growth and Neuroendocrine Hormone Levels in Carcinoid Tumor Cells. Mol Cancer Ther 2005; 4:910-917). Briefly, cells were seeded in quadruplicate on 24-well plates and incubated for 24 hours under standard conditions to allow cell attachment. The cells were then treated with valproic acid (VPA; 2-propylpentanoic acid; Sigma-Aldrich) in concentrations of 0 to 4 mM and incubated for up to 6 days. The MTT assay was performed by replacing the standard medium with 250 µL of serum-free medium containing MTT (0.5 mg/mL) and incubated at 37° C. for 3 hours. After incubation, 750 µL of dimethyl sulfoxide (DMSO; Sigma-Aldrich) was added to each well and mixed thoroughly. The plates were then measured at 540 nm using a spectrophotometer (µQuant; Bio-Tek Instruments, Winooski, Vt.).

Western Blot Analysis Carcinoid cancer cells were treated with VPA and whole cell lysates were prepared as previously described (Sippel R S et al., Raf-1 Activation Suppresses Neuroendocrine Marker and Hormone Levels in Human Gastrointestinal Carcinoid Cells. Am J Physiol Gastrointest Liver Physiol 2003; 285:G245-254). Total protein concentrations were quantified with a bicinchoninic acid assay kit (Pierce Biotechnology, Rockford, Ill.). Denatured cellular extracts were resolved by SDS-PAGE, transferred onto nitrocellulose membranes (Schleicher and Schuell, Keene, N H), blocked in milk, and incubated with appropriate antibodies. The antibody dilutions were: 1:1,000 for Notch1 (Santa Cruz Biotechnology, Santa Cruz, Calif.), mammalian achaete-scute homolog 1 (ASCL1; BD Biosciences, San Diego, Calif.), chromogranin A (Zymed Laboratories, San Francisco, Calif.), and cyclin D1 (Cell Signaling Technology, Danvers, Mass.), 1:2,000 for p21 (Cell Signaling Technology) and p27 (Santa Cruz Biotechnology), and 1:10,000 for glyceraldehyde-3-phosphate dehydrogenase (G3PDH; Trevigen, Gaithersburg, Md.). Horseradish peroxidase conjugated goat anti-rabbit or goat anti-mouse secondary antibodies (Pierce Biotechnology) were used depending on the source of the primary antibody. For visualization of the protein signal, Immunstar (Bio-Rad Laboratories, Hercules, Calif.) or SuperSignal West Femto (Pierce Biotechnology) kits were used per the manufacturer's instructions.

Flow Cytometry GI carcinoid cells treated with or without VPA were labeled for 1 hour with 10 µM bromodeoxyuridine (Sigma-Aldrich) and counter-stained with 50 µg/ml propidium iodide and analyzed by two-dimensional flow cytometry (FACSCalibur flow cytometer; BD Biosciences) to detect both fluorescein and propidium iodide as previously described (Hirai, H. et al., Involvement of cell cycle progression in survival signaling through CD40 in the B-lymphocyte line WEHI-231. Cell Death Differ 2004; 11:261-269). Results were analyzed with FlowJo software (Tree Star, Ashland, Oreg.).

Luciferase Reporter Assays GI carcinoid tumor cells were transiently transfected with luciferase constructs as previously described (Kunnimalaiyaan, M. et al., Conservation of the Notch1 signaling pathway in gastrointestinal carcinoid cells A J Physiol Gastrointest Liver Physiol 2005; 289:G636-642). Wild-type (4xwtCBF1Luc; 2 µg) or mutant (4xmutCBF1Luc; 2 µg) CBF1-luciferase reporter plasmids were co-transfected with CMV-β-gal (0.5 µg) (Hsieh J J et al., Truncated Mammalian Notch1 Activates CBF1/RBPJk-Repressed Genes by a Mechanism Resembling That of Epstein-Barr Virus EBNA2. Mol Cell Biol 1996; 16:952-959). In experiments with the γ-secretase inhibitor, N-[N-(3,5-difluorophenacetyl)-L-alanyl]-S-phenylglycine t-butyl ester (DAPT; EMD Biosciences, Darmstadt, Germany), to inhibit Notch1 cleavage and activation, cells were pretreated for 45 minutes with DAPT (50 µM) then treated with 4 mM VPA. In the second study, a plasmid containing the ASCL1 promoter construct p-3600/+37 (2 μg) was co-transfected with CMV-β-gal (0.5 μg), as previously described (Chen H et al., Conservation of the *Drosophila* Lateral Inhibition Pathway in Human Lung Cancer: a Hairy-Related Protein (HES-1) Directly Represses Achaete-Scute Homolog-1 Expression. Proc Natl Acad Sci USA 1997; 94:5355-5360). After transfection, cells were treated with or without VPA for 48 hours. Cells were harvested and lysed, and luciferase and β-galactosidase assays (Promega, Madison, Wis.) were performed in accordance with the manufacturer's instructions. Luciferase levels were measured using a Monolight 2010 Luminometer (Analytical Luminescence Laboratory, San Diego, Calif.). Luciferase activity was expressed relative to β-galactosidase activity.

Notch1 RNA Interference Assays Small-interfering RNA (siRNA) against Notch1 and non-specific siRNA (Santa Cruz Biotechnology, sc-44226 and sc-37007) were transfected into BON GI carcinoid cells using Lipofectamine 2000 (Invitrogen, San Diego, Calif.) per the manufacturer's instructions. The next day, the media containing the transfection complexes was replaced with fresh media with or without VPA (4 mM), and the cells were incubated for another 48 hours. The cells were then harvested and cell lysates were prepared for immunoblotting as described above. To determine the effect of Notch1 on carcinoid cell proliferation, BON cells were transfected with Notch1 siRNA or non-specific siRNA and incubated overnight. The next day, the cells were trypsinized, counted, and plated in equal amounts (10,000 cells per well) onto 24-well plates. On the following day, the cells were treated with control or VPA (4 mM) and the MTT assay was performed every 2 days, as described above.

Xenograft Studies BON cells ($1 \times 10^6$) were suspended in Hanks' balanced salt solution (Invitrogen) and injected subcutaneously into the right flank of 12 male nude athymic NU/NU mice (Charles River Laboratories, Wilmington, Mass.) under anesthesia. After palpable tumors developed, the mice were divided into 2 groups of 6 animals. The control group received daily intraperitoneal (i.p.) injections of saline while the treatment group received daily i.p. injections of VPA (366 mg/kg) for 20 days. The length and width of tumors were measured with a vernier caliper every 4 days and tumor volumes were calculated using the formula, volume=width$^2$×length×0.52. At the end of the experiment the mice were sacrificed and the tumors were resected and frozen in liquid nitrogen. Whole tumor cell protein lysates were prepared for immunoblotting as previously described (Vaccaro A et al., In-vivo activation of Raf-1 inhibits tumor growth and development in a xenograft model of human medullary thyroid cancer. Anticancer Drugs 2006; 17:849-853). This experiment was performed in accordance with the protocols of the University of Wisconsin Medical School Animal Care and Use Committee.

Statistical Analysis Analysis of variance (ANOVA) with Bonferroni post hoc testing was performed using a statistical analysis software package (SPSS version 10.0, SPSS, Chicago, Ill.). A P-value of <0.05 was considered significant.

Results

Valproic Acid Suppresses Growth of Carcinoid Tumor Cells In Vitro

Figure 22A:
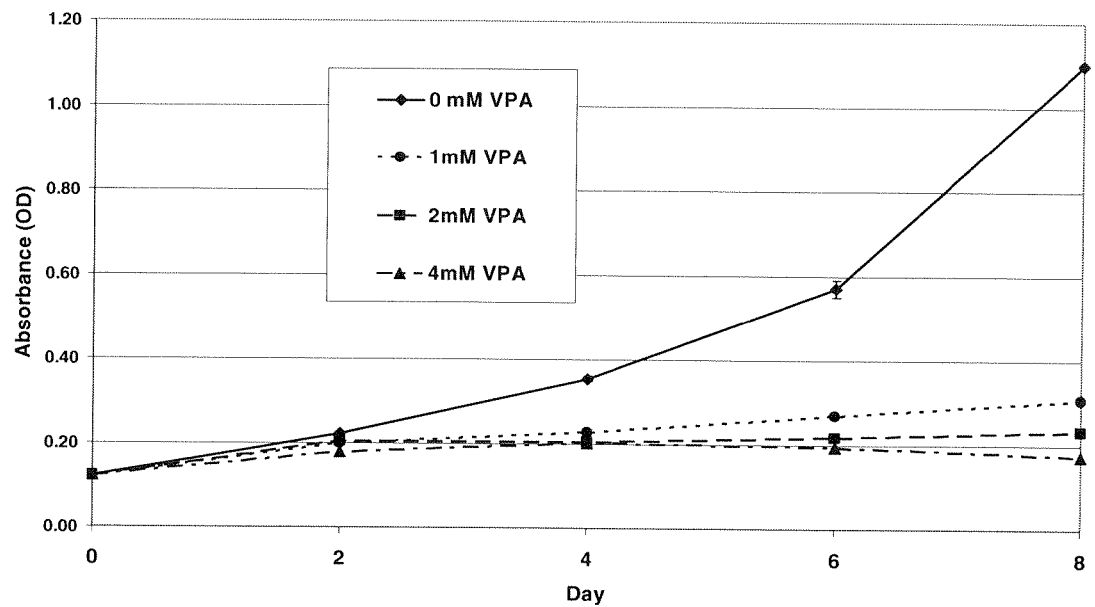
FIG. 22 shows that VPA suppresses growth of carcinoid tumor cells in vitro. Gastrointestinal (A) and pulmonary (B) carcinoid cancer cells were treated with VPA (0-4 mM) for up to 6 days and cell viability was measured with the MTT assay.
Figure 22B:
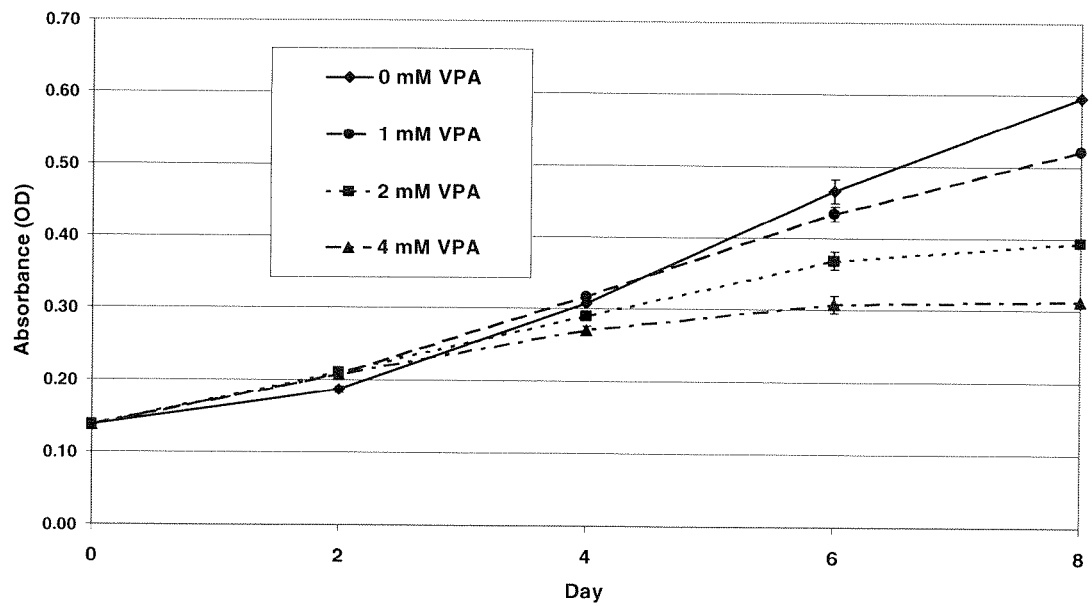

1. VPA has been shown to inhibit the growth of a variety of human cancer cells, including multiple myeloma (Kaiser M, Zavrski I, Sterz J, et al. The effects of the histone deacetylase inhibitor valproic acid on cell cycle, growth suppression and apoptosis in multiple myeloma. Haematologica 2006; 91:248-251), lymphoid cancers (Sakajiri S, Kumagai T, Kawamata N, et al. Histone deacetylase inhibitors profoundly decrease proliferation of human lymphoid cancer cell lines. Exp Hematol 2005; 33:53-61), malignant glioma (Knupfer M M, Hernaiz-Driever P, Poppenborg H, et al. Valproic acid inhibits proliferation and changes expression of CD44 and CD56 of malignant glioma cells in vitro. Anticancer Res 1998; 18:3585-3589), medulloblastoma (Li X N, Shu Q, Su J M, et al. Valproic acid induces growth arrest, apoptosis, and senescence in medulloblastomas by increasing histone hyperacetylation and regulating expression of p21Cip1, CDK4, and CMYC. Mol Cancer Ther 2005; 4:1912-1922, Shu Q, Antalffy B, Su J M, et al. Valproic Acid prolongs survival time of severe combined immunodeficient mice bearing intracerebellar orthotopic medulloblastoma xenografts. Clin Cancer Res 2006; 12:4687-4694), neuroblastoma (Stockhausen M T, Sjolund J, Manetopoulos C, et al. Effects of the histone deacetylase inhibitor valproic acid on Notch signalling in human neuroblastoma cells. Br J Cancer 2005; 92:751-759, Cinatl J, Jr, Cinatl J, Driever P H, et al. Sodium valproate inhibits in vivo growth of human neuroblastoma cells. Anticancer Drugs 1997; 8:958-963, Rocchi P, Tonelli R, Camerin C, et al. p21Waf1/Cip1 is a common target induced by short-chain fatty acid HDAC inhibitors (valproic acid, tributyrin and sodium butyrate) in neuroblastoma cells. Oncol Rep 2005; 13:1139-1144), endometrial cancer (Takai N, Desmond J C, Kumagai T, et al. Histone deacetylase inhibitors have a profound antigrowth activity in endometrial cancer cells. Clin Cancer Res 2004; 10:1141-1149), cervical cancer (Chavez-Blanco A, Perez-Plasencia C, Perez-Cardenas E, et al. Antineoplastic effects of the DNA methylation inhibitor hydralazine and the histone deacetylase inhibitor valproic acid in cancer cell lines. Cancer Cell Int 2006; 6:2-10), ovarian cancer (Takai N, Kawamata N, Gui D, et al. Human ovarian carcinoma cells: histone deacetylase inhibitors exhibit antiproliferative activity and potently induce apoptosis. Cancer 2004; 101:2760-2770), breast adenocarcinoma (Chavez-Blanco A, Perez-Plasencia C, Perez-Cardenas E, et al. Antineoplastic effects of the DNA methylation inhibitor hydralazine and the histone deacetylase inhibitor valproic acid in cancer cell lines. Cancer Cell Int 2006; 6:2-10), colon adenocarcinoma (Chavez-Blanco A, Perez-Plasencia C, Perez-Cardenas E, et al. Antineoplastic effects of the DNA methylation inhibitor hydralazine and the histone deacetylase inhibitor valproic acid in cancer cell lines. Cancer Cell Int 2006; 6:2-10), sarcoma (Chavez-Blanco A, Perez-Plasencia C, Perez-Cardenas E, et al. Antineoplastic effects of the DNA methylation inhibitor hydralazine and the histone deacetylase inhibitor valproic acid in cancer cell lines. Cancer Cell Int 2006; 6:2-10), thyroid cancer (Shen W T, Wong T S, Chung W Y, et al. Valproic acid inhibits growth, induces apoptosis, and modulates apoptosis-regulatory and differentiation gene expression in human thyroid cancer cells. Surgery 2005; 138:979-984; discussion 984-985, Catalano M G, Fortunati N, Pugliese M, et al. Valproic acid induces apoptosis and cell cycle arrest in poorly differentiated thyroid cancer cells. J Clin Endocrinol Metab 2005; 90:1383-1389), and melanoma (Valentini A, Gravina P, Federici G, et al. Valproic Acid Induces Apoptosis, p(16INK4A) Upregulation and Sensitization to Chemotherapy in Human Melanoma Cells. Cancer Biol Ther 2007; 6:185-191). However, the effects of VPA on carcinoid tumor cell growth have not been characterized to date. We utilized the MTT assay to measure cell viability after VPA treatment of BON GI and H727 pulmonary human carcinoid tumor cells. GI carcinoid cells treated with VPA had a profound dose-dependent inhibition of growth (FIG. 22A). After 6 days of treatment, growth of cells exposed to 1 mM of VPA was inhibited by 50% relative to untreated cells. Statistically significant growth inhibition was also seen in pulmonary carcinoid cells treated with VPA (FIG. 22B).

A Mechanism of VPA-Induced Carcinoid Growth Suppression is Cell Cycle Arrest

Figure 23A:
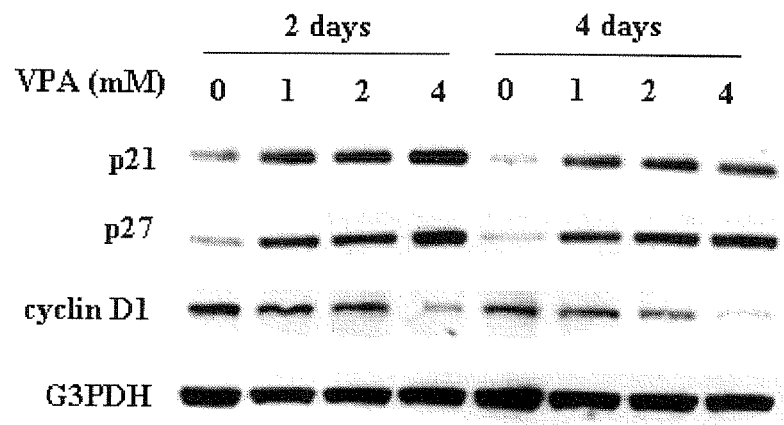
FIG. 23 shows that a mechanism of VPA-induced growth inhibition is cell cycle arrest. A, Western blot analysis was performed on VPA-treated GI carcinoid cancer cells to measure protein expression of cell cycle regulators p21, p27, and cyclin D1. G3PDH was used as a loading control. B, flow cytometry was performed on GI carcinoid cells to measure the proportion of cells in each cell cycle phase.
Figure 23B:
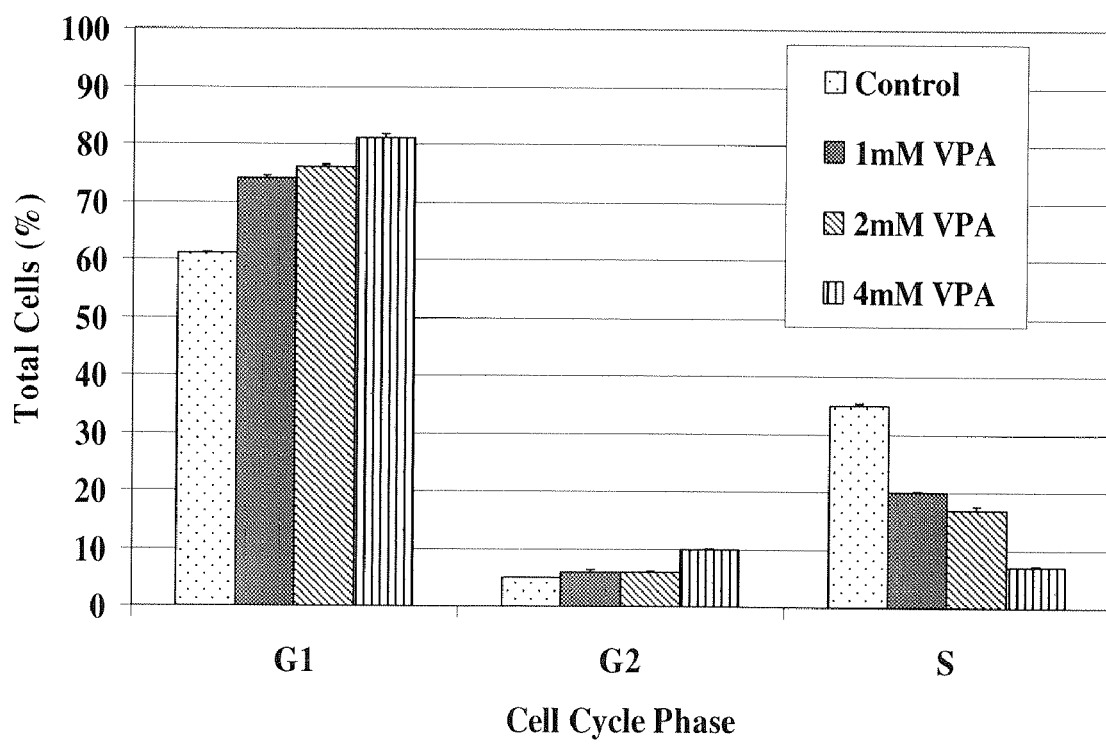

After establishing that VPA inhibits cell proliferation in carcinoids, we were interested in determining the mechanism of action for this effect. Previously, VPA has been shown to induce cell cycle arrest in a variety of cancer cell lines by modulating expression of p21 and other regulatory proteins (Kaiser M, Zavrski I, Sterz J, et al. The effects of the histone deacetylase inhibitor valproic acid on cell cycle, growth suppression and apoptosis in multiple myeloma. Haematologica 2006; 91:248-251, Li X N, Shu Q, Su J M, et al. Valproic acid induces growth arrest, apoptosis, and senescence in medulloblastomas by increasing histone hyperacetylation and regulating expression of p21Cip1, CDK4, and CMYC. Mol Cancer Ther 2005; 4:1912-1922, Rocchi P, Tonelli R, Camerin C, et al. p21Waf1/Cip1 is a common target induced by short-chain fatty acid HDAC inhibitors (valproic acid, tributyrin and sodium butyrate) in neuroblastoma cells. Oncol Rep 2005; 13:1139-1144, Catalano M G, Fortunati N, Pugliese M, et al. Valproic acid induces apoptosis and cell cycle arrest in poorly differentiated thyroid cancer cells. J Clin Endocrinol Metab 2005; 90:1383-1389). We performed Western blot analysis using BON cell lysates after 2 day and 4 day treatment with VPA to measure the effect of the drug on cell cycle regulators. Treatment of BON cells with 1 mM of VPA resulted in an increase in protein levels of the cyclin-dependent kinase inhibitors p21 and p27 (FIG. 23). The cell cycle promoter cyclin D1 was suppressed by VPA, with levels almost undetectable after 4 days treatment with 4 mM of VPA. Similar results on expression of p21, p27, and cyclin D1 were seen in H727 cells treated with VPA (data not shown). To confirm the induction of cell cycle arrest with VPA treatment, we performed flow cytometry. VPA treatment of BON cells resulted in a dose-dependent increase in the percentage of cells in the G1 phase of the cell cycle, accompanied by a decrease in cells in the S phase (FIG. 23). Taken together, these immunoblot and flow cytometry data indicate that VPA inhibits carcinoid cell growth by inducing G1 phase cell cycle arrest.

VPA Decreases Levels of Chromogranin A

Figure 24A:
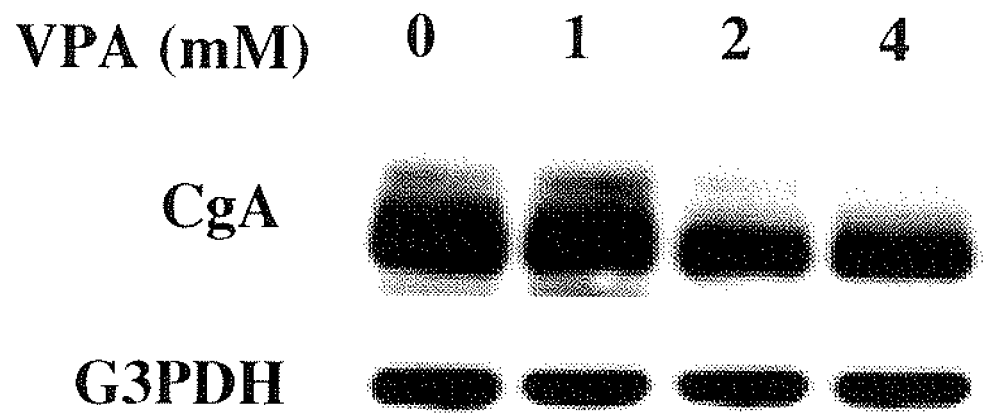
FIG. 24 shows that VPA decreases levels of chromogranin A in carcinoid cells. Western blot analysis of GI (A) and pulmonary (B) carcinoid cells for protein expression of the neuroendocrine tumor marker chromogranin A (CgA) after 2 days treatment with VPA. G3PDH was used to confirm equal protein loading.
Figure 24B:
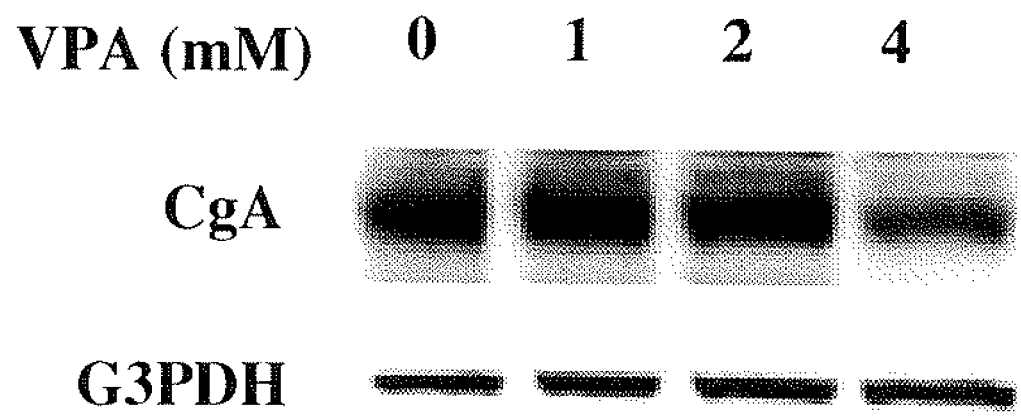

Neuroendocrine tumors such as carcinoids frequently cause debilitating symptoms in patients due to excess tumor secretion of various bioactive amines and peptides. Chromogranin A (CgA) is an acidic glycoprotein that is co-secreted with hormones such as serotonin by carcinoid tumors. All neuroendocrine tumors produce CgA, and the protein is thus a useful marker for this class of malignancies. We were interested in whether VPA had the ability to alter the neuroendocrine phenotype in carcinoid tumor cells, so we performed Western analysis for expression of CgA. After two days treatment of GI (FIG. 24A) and pulmonary (FIG. 24B) carcinoid cancer cells with VPA, protein levels of CgA decreased, indicating a change in the neuroendocrine phenotype of these tumor cells.

VPA Activates Notch1 Signaling in Carcinoid Cells

After establishing that VPA inhibits carcinoid cell growth and suppresses production of CgA, we wanted to identify the mechanism of action for these effects. We have previously shown that Notch1 signaling is absent at baseline in neuroendocrine tumors, and that Notch1 overexpression with an inducible Notch1 construct causes inhibition of cell growth and hormone production (Kunnimalaiyaan, M. et al., "Conservation of the Notch1 Signaling Pathway in Gastrointestinal Carcinoid Cells," Am J Physiol Gastrointest Liver Physiol 289:G636-642 (2005), Kunnimalaiyaan, M. Et al., "Overexpression of the NOTCH1 Intracellular Domain Inhibits Cell Proliferation and Alters the Neuroendocrine Phenotype of Medullary Thyroid Cancer Cells," J Biol Chem 281:39819-39830 (2006)). Based on a recent report describing the ability of VPA to increase Notch1 protein levels in neuroblastoma cells (Stockhausen M T, Sjolund J, Manetopoulos C, et al. Effects of the histone deacetylase inhibitor valproic acid on Notch signalling in human neuroblastoma cells. Br J Cancer 2005; 92:751-759), and our previous research on negative regulation of achaete-scute complex-like 1 (ASCL1) by Notch1, we hypothesized that VPA might also activate Notch1 signaling in carcinoid cells, with anti-tumor effects.

Figure 25A:
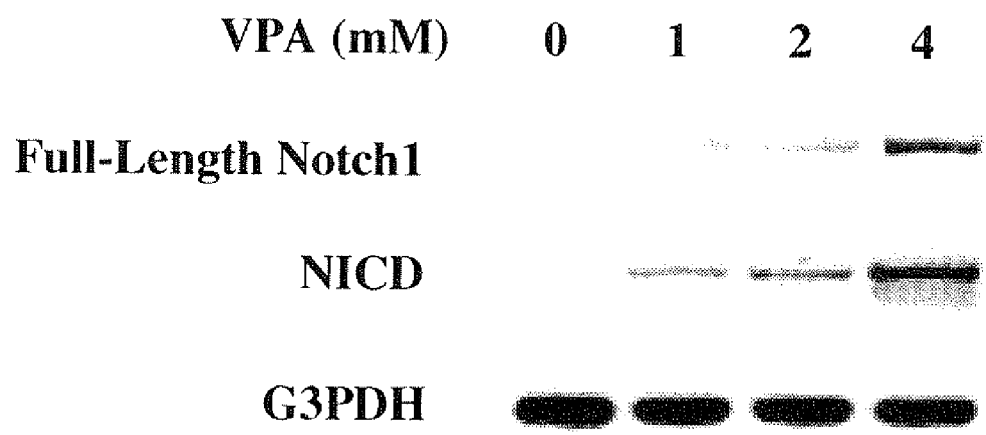
FIG. 25 shows that VPA activates Notch1 in carcinoid cells. GI (A) and pulmonary (B) carcinoid cancer cells were treated with VPA (0-4 mM) for 2 days and cell lysates were immunoblotted for full-length Notch1 and the active Notch1 intracellular domain (NICD). Equal loading was confirmed with G3PDH.
Figure 25B:
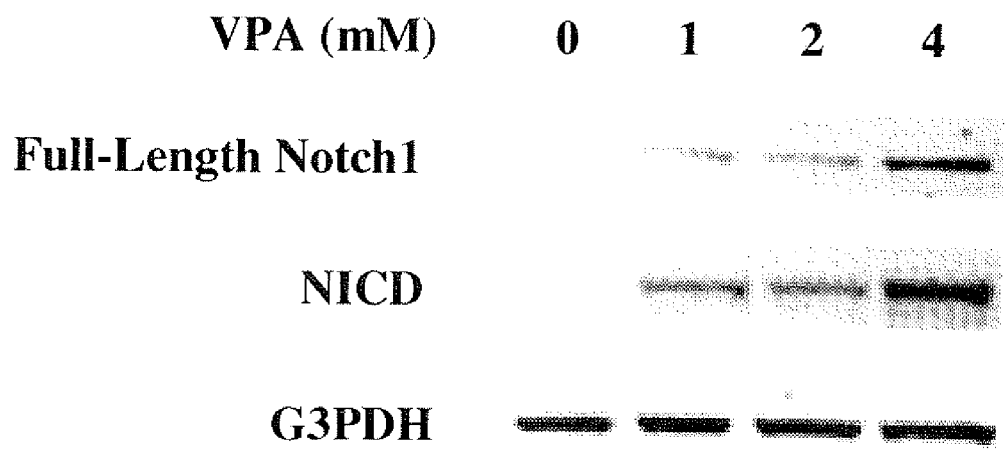
Figure 26A:
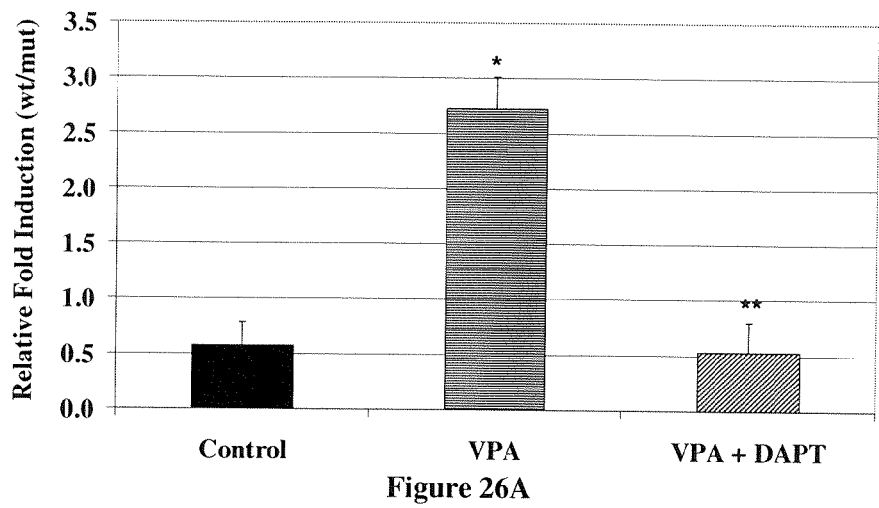
FIG. 26 shows that VPA-induced Notch1 is functionally active. A, GI carcinoid cells were transiently transfected with a luciferase reporter containing the CBF1 binding site (wild-type or mutant) as well as a CMV-β-galactosidase plasmid and then treated with VPA with or without the γ-secretase inhibitor DAPT. Relative luciferase activity (wild-type/mutant) relative to β-galactosidase expression is shown. Immunoblot analysis of GI (B) and pulmonary (C) carcinoid cells treated with VPA for achaete-scute complex-like 1 (ASCL1), a neuroendocrine transcription factor well-known to be negatively regulated by Notch1. D, GI carcinoid cells were transfected with an ASCL1-luciferase reporter plasmid and a CMV-β-galactosidase control plasmid and treated with or without VPA. Luciferase activity relative to β-galactosidase activity is shown.

2. To assess the effect of VPA on Notch1 protein expression, we performed Western blot analysis. There was a lack of Notch1 at baseline in the two carcinoid cell lines. Interestingly, VPA treatment of GI (FIG. 25A) and pulmonary (FIG. 25B) carcinoid cells led to an increase in both full-length Notch1 and NICD, the active form of the protein. We next asked, is the Notch1 induced by VPA functionally active? Notch1 is activated by a series of proteolytic cleavage events, mediated by γ-secretase and other enzymes, resulting in the liberation of NICD. NICD then translocates into the nucleus, where it binds with centromere-binding factor 1 (CBF1) and other proteins to form a DNA-binding complex. This complex activates transcription of target genes such as hairy enhancer of split 1(HES-1) (Chen H, Biel M A, Borges M W, et al. Tissue-specific expression of human achaete-scute homologue-1 in neuroendocrine tumors: transcriptional regulation by dual inhibitory regions. Cell Growth Differ 1997; 8:677-686, Artavanis-Tsakonas S, Rand M D, Lake R J. Notch signaling: cell fate control and signal integration in development. Science 1999; 284:770-776, Allenspach E J, Maillard I, Aster J C, et al. Notch signaling in cancer. Cancer Biol Ther 2002; 1:466-476, Bray S J. Notch signalling: a simple pathway becomes complex. Nat Rev Mol Cell Biol 2006; 7:678-689). We used a luciferase reporter assay incorporating the CBF1 binding site to measure the functional activity of Notch1 induced by VPA (Hsieh J J, Henkel T, Salmon P, et al. Truncated mammalian Notch1 activates CBF1/RBPJk-repressed genes by a mechanism resembling that of Epstein-Barr virus EBNA2. Mol Cell Biol 1996; 16:952-959). VPA treatment of GI carcinoid cells trasfected with this construct resulted in a 5-fold increase in luciferase activity (FIG. 26A). Importantly, the γ-secretase inhibitor DAPT blocked the effect of VPA on CBF1 binding, indicating that the increase in CBF1 binding was due to induction of NICD.

Figure 26B:
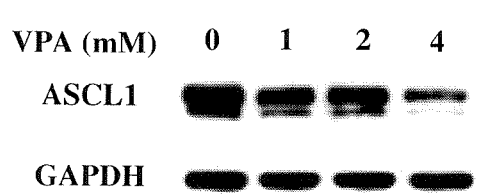
Figure 26C:
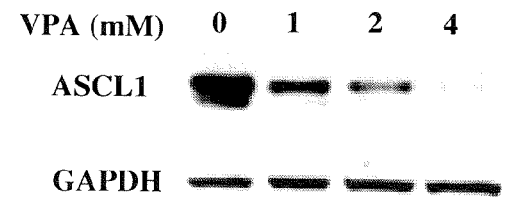
Figure 26D:
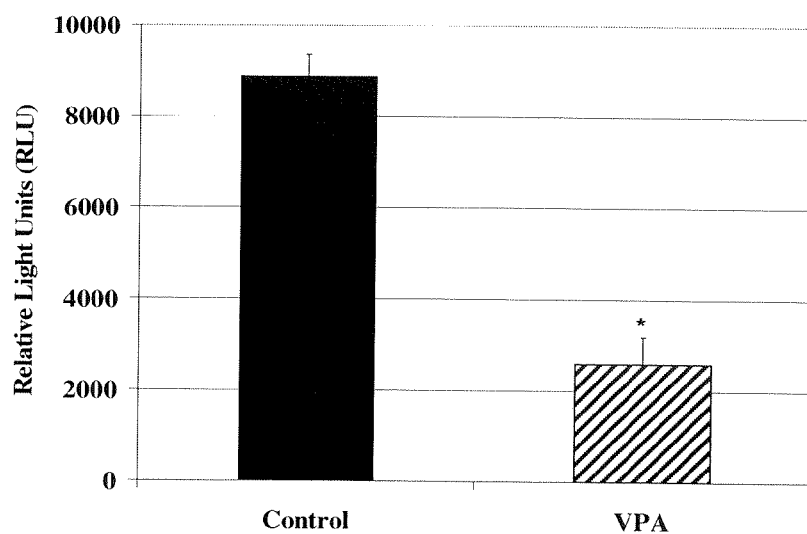

3. We have previously shown that activation of Notch1 signaling in carcinoid cells results in suppression of ASCL1, a basic helix-loop-helix transcription factor that regulates the neuroendocrine phenotype (Kunnimalaiyaan, M. et al., "Conservation of the Notch1 Signaling Pathway in Gastrointestinal Carcinoid Cells," Am J Physiol Gastrointest Liver Physiol 289:G636-642 (2005), Nakakura, E. K et al., "Regulation of Neuroendocrine Differentiation in Gastrointestinal Carcinoid Tumor Cells by Notch Signaling," J Clin Endocrinol Metab 90:4350-4356 (2005)). If VPA is able to activate Notch1 signaling in carcinoids, therefore, we would expect to see a decrease in expression of ASCL1. Western blot analysis of VPA-treated GI (FIG. 26B) and pulmonary (FIG. 26C) carcinoid cancer cells showed a dose-dependent decrease in ASCL1 protein. Exposure of H727 cells to 4 mM of VPA for 2 days suppressed ASCL1 to undetectable levels. To determine the mechanism of VPA-mediated suppression of ASCL1, we utilized an ASCL1 promoter construct [14]. As expected, at baseline, GI carcinoid cells bearing this construct had a high level of luciferase activity. However, VPA treatment caused an almost 4-fold decrease in luciferase activity, indicating transcriptional repression of ASCL1 (FIG. 26D). Thus, VPA treatment led to a significant reduction in ASCL1 transcription. Since Notch1 is known to silence ASCL1 transcription, this provides further evidence that VPA-mediated ASCL1 reduction is through Notch1 signaling.

Notch1 RNA Interference Blocks the Effects of VPA in Carcinoid Cells

Figure 27A:
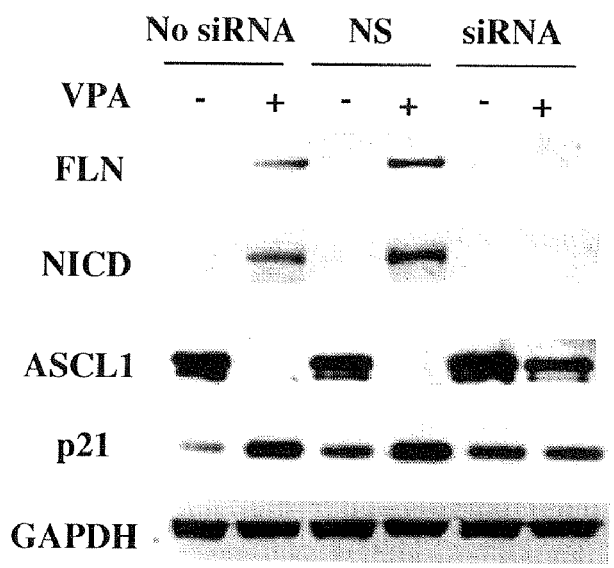
FIG. 27 shows that Notch1 RNA interference blocks the effects of VPA in carcinoid cells. A, Western blot analysis of GI carcinoid cells transfected with Lipofectamine (siRNA: None), non-specific (NS) siRNA, or Notch1 siRNA, and then treated with or without VPA, for expression of full-length Notch1, NICD, ASCL1, and p21. B, MTT cellular proliferation assay of GI carcinoid cells transfected with Lipofectamine (siRNA: None) or Notch1 siRNA and treated with or without VPA for 4 days.

4. VPA has diverse biological effects. Besides Notch1 signaling, VPA is known to influence Akt (Chen J, Ghazawi F M, Bakkar W, et al. Valproic acid and butyrate induce apoptosis in human cancer cells through inhibition of gene expression of Akt/protein kinase B. Mol Cancer 2006; 5:71-82), GSK-3β (Chen G, Huang L D, Jiang Y M, et al. The mood-stabilizing agent valproate inhibits the activity of glycogen synthase kinase-3. J Neurochem 1999; 72:1327-1330), inositol (O'Donnell T, Rotzinger S, Nakashima T T, et al. Chronic lithium and sodium valproate both decrease the concentration of myo-inositol and increase the concentration of inositol monophosphates in rat brain. Brain Res 2000; 880:84-91, Vaden D L, Ding D, Peterson B, et al. Lithium and valproate decrease inositol mass and increase expression of the yeast INO1 and INO2 genes for inositol biosynthesis. J Biol Chem 2001; 276:15466-15471, Williams R S, Cheng L, Mudge A W, et al. A common mechanism of action for three mood-stabilizing drugs. Nature 2002; 417:292-295), angiogenesis factors (Michaelis M, Michaelis U R, Fleming I, et al. Valproic acid inhibits angiogenesis in vitro and in vivo. Mol Pharmacol 2004; 65:520-527), and HDAC enzymes (Gottlicher M, Minucci S, Zhu P, et al. Valproic acid defines a novel class of HDAC inhibitors inducing differentiation of transformed cells. EMBO J 2001; 20:6969-6978, Phiel C J, Zhang F, Huang E Y, et al. Histone deacetylase is a direct target of valproic acid, a potent anticonvulsant, mood stabilizer, and teratogen. J Biol Chem 2001; 276:36734-36741, Gurvich N, Tsygankova O M, Meinkoth J L, et al. Histone deacetylase is a target of valproic acid-mediated cellular differentiation. Cancer Res 2004; 64:1079-1086). In order to confirm that the effects of VPA on carcinoid cells—i.e., inhibition of growth, induction of cell cycle arrest, and suppression of neuroendocrine tumor markers—are due to activation of Notch1 signaling, we utilized RNA interference. BON GI carcinoid cells were transiently transfected with siRNA against Notch1, non-specific siRNA, or vehicle (Lipofectamine) alone, and cell lysates were analyzed by immunoblotting. In the absence of siRNA, VPA treatment led to an increase in Notch1 and p21, and a decrease in ASCL1 (FIG. 27A, lane 2). Similar results were obtained in the presence of non-specific siRNA (FIG. 27A, lane 4). Blockade of VPA-mediated Notch1 induction was achieved with Notch1 siRNA. Importantly, the abrogation of Notch1 induction with siRNA reversed the VPA-mediated changes in ASCL1 and p21 expression (FIG. 27A, lane 6).

Figure 27B:
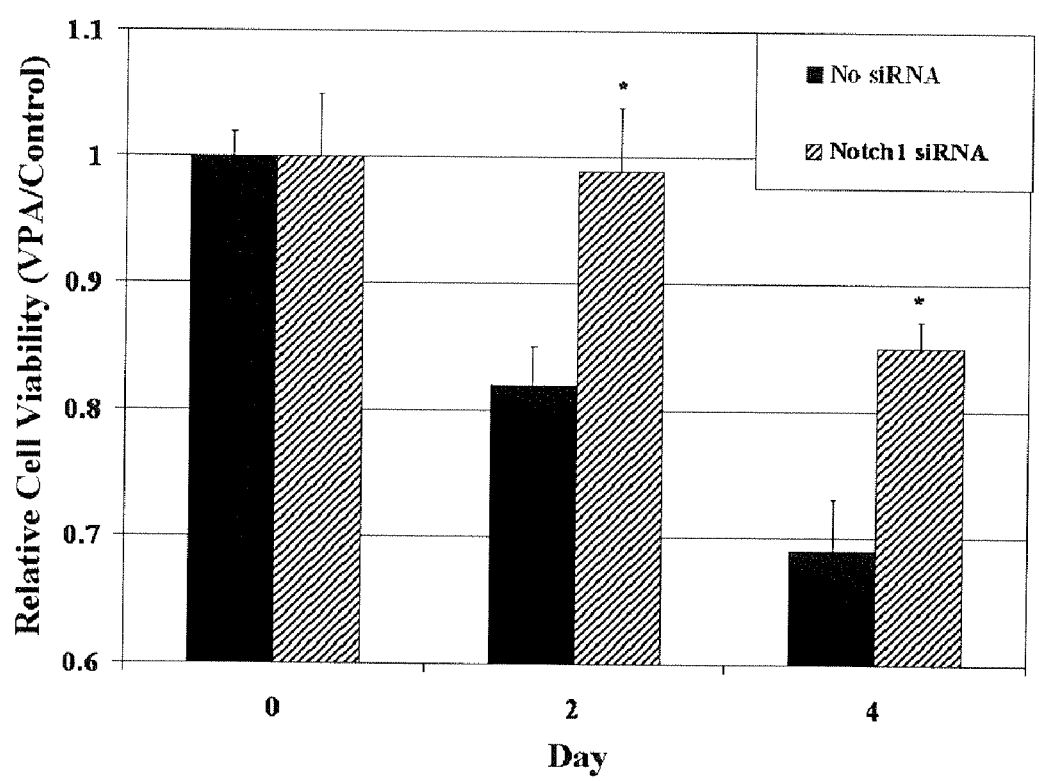

We next assessed the impact of Notch1 siRNA on carcinoid cell growth in combination with VPA treatment. BON cells were again transfected with anti-Notch1 siRNA or controls, treated with or without VPA, and the MTT cell proliferation assay was performed. Cells transfected with siRNA against Notch1 were partially protected from the anti-proliferative effect of VPA (FIG. 27B). The difference in relative cell viability between cells transfected with Notch1 siRNA and controls was statistically significant. This suggests that the growth inhibition seen with VPA treatment is mediated in part by Notch1 signaling.

VPA Inhibits the Growth of Carcinoid Tumors In Vivo

Figure 28A:
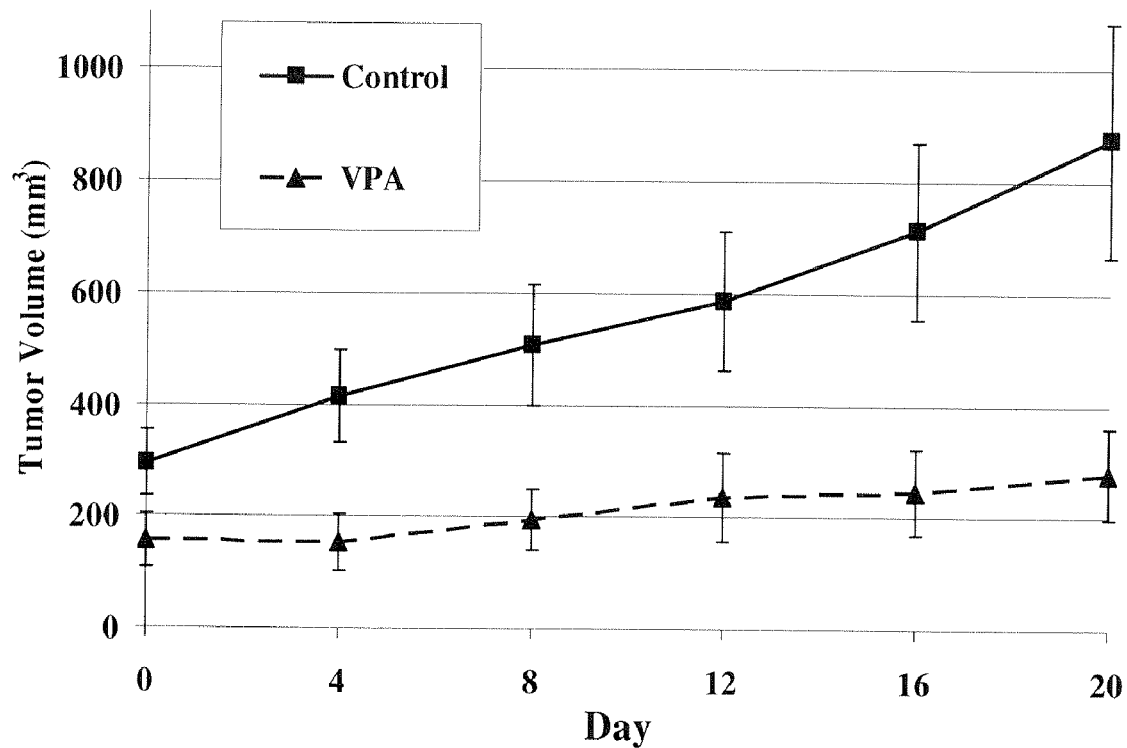
FIG. 28 shows that VPA inhibits the growth of carcinoid tumors and suppresses ASCL1 in vivo. Subcutaneous GI carcinoid tumors were developed in immunocompromised mice, which were then given daily intraperitoneal injections of VPA or saline (control). A, tumor volume in VPA-treated and control animals. B, immunoblotting of resected tumor cell extracts for protein levels of the Notch1 signaling target, neuroendocrine tumor maker ASCL1.

After confirming that VPA activates Notch1 signaling and suppresses carcinoid cell growth in vitro, we were interested in testing its efficacy in vivo. Subcutaneous human GI carcinoid tumors were developed in immunocompromised mice, which were then given daily intraperitoneal injections of VPA, and the tumors were measured every 4 days for 20 days. The tumors of the saline-treated control mice grew at a higher rate than did those of the VPA-treated animals (FIG. 28A). Indeed, the growth of the tumors in the treatment group was almost static. On the last day of the experiment, blood was drawn from each animal in the treatment group two hours after intraperitoneal injection of VPA. Significantly, the median serum VPA level was 46 μg/mL, which is below the therapeutic range of 50-125 μg/mL commonly used for human patients treated with VPA for epilepsy.

Figure 28B:
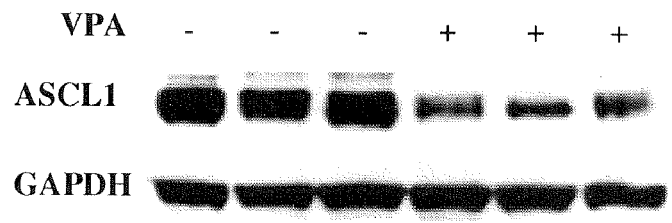

After the animals were sacrificed, the tumors were resected and frozen, and protein was isolated for Western blot analysis. As shown in FIG. 28B, tumors from the VPA-treated mice had decreased expression of ASCL1 compared to controls. As ASCL1 is an established target of Notch1 signaling [6], the down-regulation of ASCL1 seen in the VPA-treated tumors provides evidence that systemically-administered VPA is able to activate Notch1 signaling in carcinoid tumors in vivo.

The data above show that carcinoids in vitro, we also report the results of a mouse xenograft experiment. Carcinoid tumors in mice treated with VPA exhibited a markedly decreased rate of growth compared to controls. Importantly, peak VPA serum levels in the treated animals were well below the upper limit of the therapeutic range for human patients treated with VPA for epilepsy, and no signs of neurotoxicity were seen in the mice. Furthermore, Western blot analysis of the resected tumors demonstrated suppression of ASCL1 in the VPA-treated group. As ASCL1 is a well-established target of Notch1 signaling, the ability of non-toxic concentrations of VPA to decrease levels of ASCL1 provides important evidence that systemically administered VPA can activate Notch1 in carcinoid tumors in vivo.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

What is claimed is:

1. A method for inhibiting growth or neuroendocrine hormone production of a gastrointestinal (GI) carcinoid cancer cell which comprises an endogenous Notch1 gene, the method comprising increasing the level of expression product of the endogenous Notch1 gene of the GI carcinoid cancer cell, by contacting the GI carcinoid cancer cell with an effective amount of valproic acid (VPA), wherein growth or neuroendocrine hormone production of the GI carcinoid cancer cell is inhibited.

2. The method according to claim 1, wherein the GI carcinoid cancer cell is an advanced stage GI carcinoid cancer cell.

3. A method for inhibiting in a mammal the growth or neuroendocrine hormone production of a gastrointestinal (GI) carcinoid cancer cell which comprises an endogenous Notch1 gene, wherein the method comprises administering an effective amount of valproic acid (VPA) to the mammal, wherein the level of expression product of the endogenous Notch1 gene of the GI carcinoid cancer cell is increased, or wherein the growth or neuroendocrine hormone production of the GI carcinoid cell is inhibited.

4. The method according to claim 3, wherein the GI carcinoid cancer cell is an advanced stage GI carcinoid cancer cell.

5. The method according to claim 3, wherein the mammal is treated with a daily intraperitoneal injection of VPA at a dosage of about 366 mg VPA/kg bodyweight.

6. The method according to claim 3, wherein serum concentration of VPA in the mammal reaches a concentration of about 46 µg/ml two hours after intraperitoneal injection of VPA.

* * * * *